(12) United States Patent
Chan et al.

(10) Patent No.: US 10,738,104 B2
(45) Date of Patent: *Aug. 11, 2020

(54) ANTIBODIES AGAINST F GLYCOPROTEIN OF HENDRA AND NIPAH VIRUSES

(71) Applicant: The Henry M. Jackson Foundation for the Advancement of Military Medicine, Inc., Bethesda, MD (US)

(72) Inventors: Yee-Peng Chan, Bethesda, MD (US); Christopher C. Broder, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/951,327

(22) Filed: Apr. 12, 2018

(65) Prior Publication Data

US 2018/0298081 A1    Oct. 18, 2018

Related U.S. Application Data

(62) Division of application No. 15/112,913, filed as application No. PCT/US2015/012641 on Jan. 23, 2015, now Pat. No. 9,982,038.

(60) Provisional application No. 61/931,006, filed on Jan. 24, 2014.

(51) Int. Cl.
*C07K 16/10* (2006.01)

(52) U.S. Cl.
CPC ...... *C07K 16/1027* (2013.01); *C07K 2317/21* (2013.01); *C07K 2317/24* (2013.01); *C07K 2317/34* (2013.01); *C07K 2317/51* (2013.01); *C07K 2317/55* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS 9,982,038 B2 * 5/2018 Chan ................. C07K 16/1027
2018/0298081 A1 * 10/2018 Chan ................. C07K 16/1027

OTHER PUBLICATIONS

Xiang et al. (Journal of Molecular Biology. 1995; 253: 385-390).*
Zabetakis et al. (PLoS One vol. 8, No. 10, e77678, 2013).*
MacCallunn et al. J. Mol. Biol. (1996) 262, 732-745.*
Kashmiri et al. (Methods. 2005; 36:25-34).*
Anonymous, ScienceDaily www.sciencedaily.com/releases/2015/05/150504120513. Retrieved Dec. 7, 2015 Human clinical trials begin for deadly Hendra virus therapy; 2015.*
Wong et al. (PNAS. Jan. 2016: 113 (4): 1056-1061).*

* cited by examiner

*Primary Examiner* — Shanon A. Foley
(74) *Attorney, Agent, or Firm* — Morgan, Lewis & Bockius LLP

(57) ABSTRACT

The present invention relates to antibodies or antibody fragments that bind, neutralize, and/or inhibit Hendra or Nipah virus. The invention provides antibodies or antibody fragments that selectively bind to the F glycoprotein of Hendra or Nipah virus, and pharmaceutical compositions including such antibodies and/or fragments. The invention further provides polynucleotides encoding the antibodies and fragments of the invention and host cells transformed therewith. Additionally, the invention discloses prophylactic, therapeutic, and diagnostic methods employing the antibodies, fragments, polynucleotides, and/or compositions of the invention.

16 Claims, 9 Drawing Sheets
Specification includes a Sequence Listing.

m5B3 VL

FR1 — D I Q M T Q S P A S Q S A S L G E S V T I T C
CDR-L1 — L A S Q T I G T W L A
— W Y Q Q K

FR2 — P G K S P Q L L I Y
CDR-L2 — A A T S L A D
FR3 — G V P S R F S G S G S G T K F S F K I S S L Q A E D F V S Y Y C
CDR-L3 — Q Q F Y S T P F T
FR4 — G G G T K L E I K R m5B3 VH

FR1 — E V Q L V E S G G G L V K P G G S L K L S C A A S
CDR-H1 — G F T F S S Y D M S
— W V R Q

FR2 — T P E K R L E W V A M I
CDR-H2 — S S G G S Y S Y Y P D S V K G
FR3 — R F T I S R D N A K N T L Y L Q M S S L R S E D T A M Y Y C A R
CDR-H3 — Q G D Y A W F A Y
FR4 — W G Q G T L V T V S

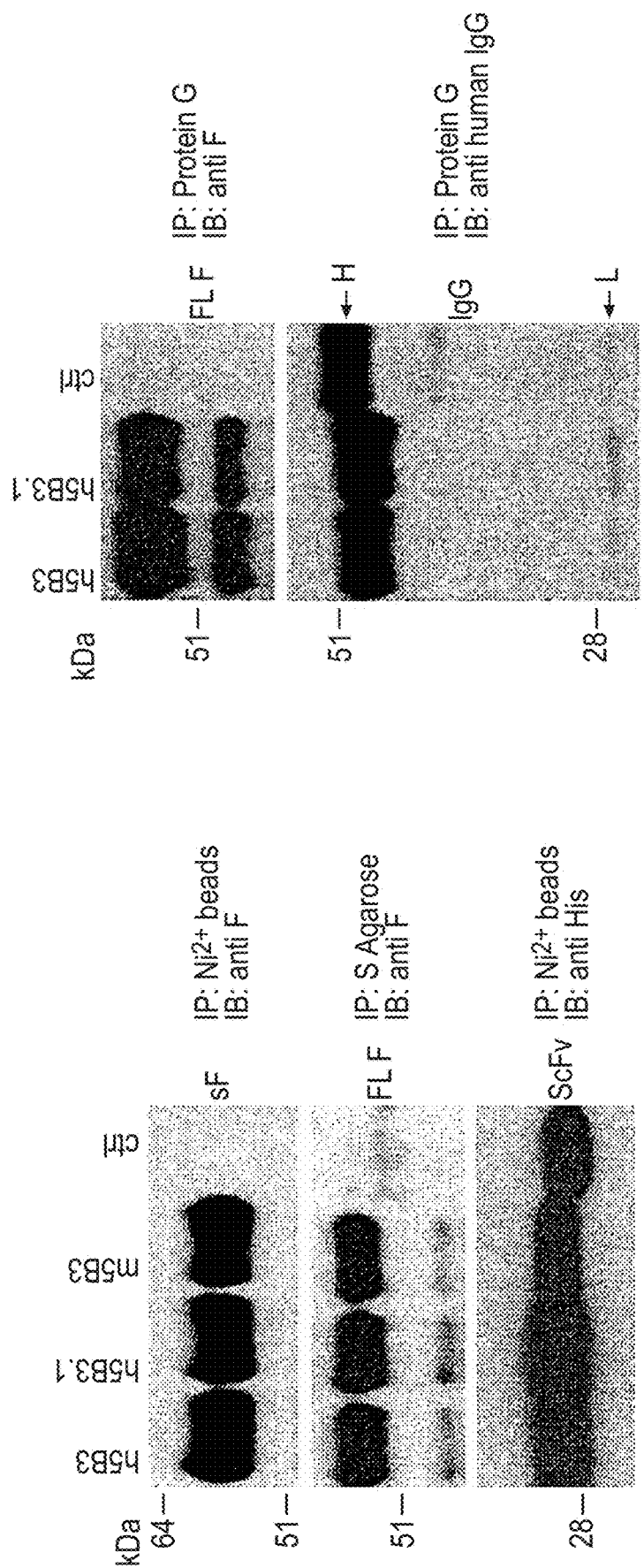

VH FR

| | |
|---|---|
| h5B3 | EVQLVESGGGLVKPGGSLRLSCAASWVRQAPGKGLEWVARFTISRDNSKNTLYLQMNSLRAEDTAVYYCARWGQGTLVTVS |
| m5B3 | EVQLVESGGGLVKPGGSLKLSCAASWVRQTPEKRLEWVARFTISRDNAKNTLYLQMSSLRSEDTAMYYCARWGQGTLVTVS | human
ScFv
library

```
EVQLVESGGGLVKPGGSLRLSCAASWVRQAPGKGLEWVARFTISRDNSKNTAYLQMNSLKSDDPAVYYCTRWGQGTLVTVS
EVQLVESGGGLVKPGGSLRLSCAASWVRQAPGKGLEWVGRFTISRDDSKSIAYLQMNSLRTEDTAVYYCTRWGQGTLVTVS
EVQLVESGGGVQPGRSLRLSCAASWVRQAPGKGLEWVGRFSISRDNARNSLYLQMNSLRDDDTSVYYCVRWGQGTLVTVS
EVQLVESGGGPGQAWGVLRLSCAASWVRQAPGKGLEWVSRFTISRDNARNSLYLQMNSLRDDDTSVYYCVRWGQGTLVTVS
EVQLVESGAEVKKPGESLKISCKGSWVRQMPGKGLEWMGQVTISADKSITTAYLQWSSLKASDTAMYCARWGQGTPVTVS
EVQLVESGGGVVQPGRSLRLSCAASWVRQAPGKGLEWVARFTISRDNSKNTLYLQMNSLRAEDTAVYYCARWGQGTLVTVS
EVQLVESGAEVKRPGASVKVSCKAASWVRQAPGQGLEWMGRVTMTTETSTSTAYMELRSLRSDDTAVYYCARWGQGTLVTVS
EVQLVESGGGLVQPGGSLRLSCAASWVRQAPGKGLEWVSRFTISRDNSKNTLFLQMNSLRAEDTAVYYCATWGQGTLVTVS
EVQLVESGGGLVQPGGSLRLSCAASWVRQAPGKGLEWVARFSISRDNARNSLYLQMNSLRDDDTSVYYCVRWGQGTLVTVS
EVQLVESGGGVVQPGRSLRLSCAASWVRQAPGKGLEWVSRFTISRDNSKNTLYLQMNSPRAEDTAVYYCAKWGQGTLVTVS
EVQLVESGGGLVKPGGSLRLTCAASWVRQAPGKGLEWVARFTISRDNSENMLYLQMNSLRAEDTAVYYCAKWGQGTLVTVS
EVQLVESGGGLVKPGGSLRLSCAASWVRQAPGKGLEWVSRFTISRDNAKNSLYLQMNSLRAEDTAVYYCAKWGQGTLVTVS
```

VL FR

| | |
|---|---|
| h5B3 | DIQMTQSPSSLSASVGDRVTITCLAWYQQKPGKAPKLLIYGVPSRFSGSGSGTDFTLTISSLQPEDFATYYCTFGQGTKLEIK |
| m5B3 | DIQMTQSPASQSASLGESVTITCLAWYQQKPGKSPQLLIYGVPSRFSGSGSGTKFSFKISSLQAEDFVSYCTFGGGTKLEIK | human
ScFv
library

```
DIQMTQSPSSLSASVGDRVTITCLNWYQQKPGKAPKLLIYGVPSRFSGSGSGTEFTLTISSLQPEDFATYYCTFGQGTKLEIK
DIQMTQSPSFLSASVGDRVTITCLNWYQQKPGKAPKLLIYGVPSRFSGSGSGTDFTLTISSLQPEDFATYYCTFGQGTKLEIK
DIQMTQSPSTLSASVGDRVTITCLNWYQQRPGKAPKLLIYGVPSRFSGSGSGTDFTLTISSLQPEDFATYYCTFGQGTKLEIK
DIQMTQSPSSLSASVGDRVTITCLNWYQQKPGKAPKLLIYGVPSRFSGSGSGTDFTLTISSLQPEDFATYYCTFGQGTKLEIK
DIQMTQSPSFSASTGDRVTITCLNWYQQKPGKAPKLLIYGVPSRFSGSGSGTEFTLTISSLQPEDFATYYCTFGQGTKLEIK
DIQMTQSPSSLSASVGDRVTITCLNWYQQKPGKAPKLLIYGVPSRFSGSGSGTDFALTISSLQPEDFALTISSLQPEDFATYYCTFGQGTKLEIK
DIQMTQSPSSLSASVGDRVTITCLNWYQQKPGKAPKLLIYGVPSRFSGSGSGTEFTLTISSLQPEDFATYYCTFGQGTKLEIK
DIQMTQSPSSLSASIGDRVTITCLNWYQQRPGKAPKLLIYGVPSRFSGSGSGTDFTLTISSLQPEDFATYYCTFGQGTKLEIK
DIQMTQSPSSLSASVGDRVTITCLNWYQQKPGRAPKLLIYGVPSRFSGSGSGTDFTLTISSLQPEDFAAYFCTFGQGTKLEIK
DIQMTQSPSSLSASVGDRVTITCLNWYQQKPGKAPKLLIYGVPSRFSGSGSGTDFTLTISSLQPEDFATYYCTFGRGTKLEIK
DIQMTQSPSSLSASVGDRVTITCLNWYQQKPGKAPKLLIYGVPSRFSGSGSGTEFFTLTISSLQPEDFATYFCTFGQGTKLEIK
```

FIG. 3A h5B3.1 VH

```
       FR1                            CDR-H1
EVQLVESGGGLVKPGGSLRLSCAASGFTFSSYSMSWVRQ
    FR2              CDR-H2              FR3
APGKGLEWVAMISSGGSYSYYADSVKGRFTISRDNSKNT
                            CDR-H3    FR4
LYLQMNSLRAEDTAVYYCARQGDYAWFDIWGQGTLVTVS
```

FIG. 3B

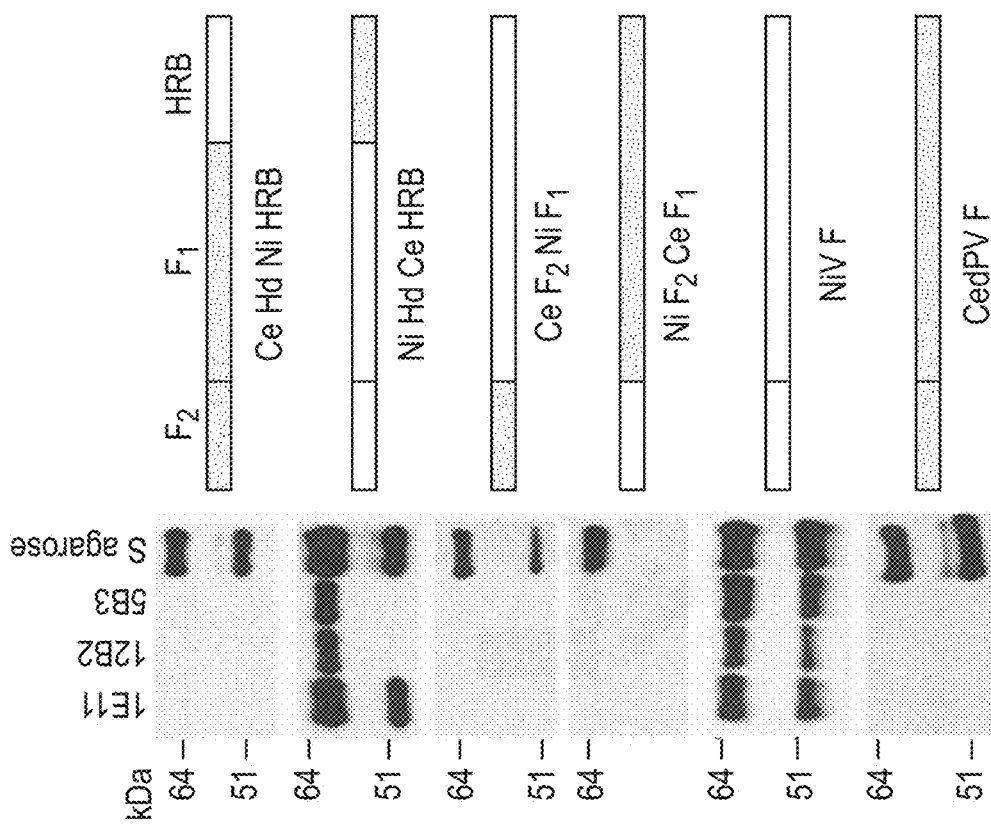
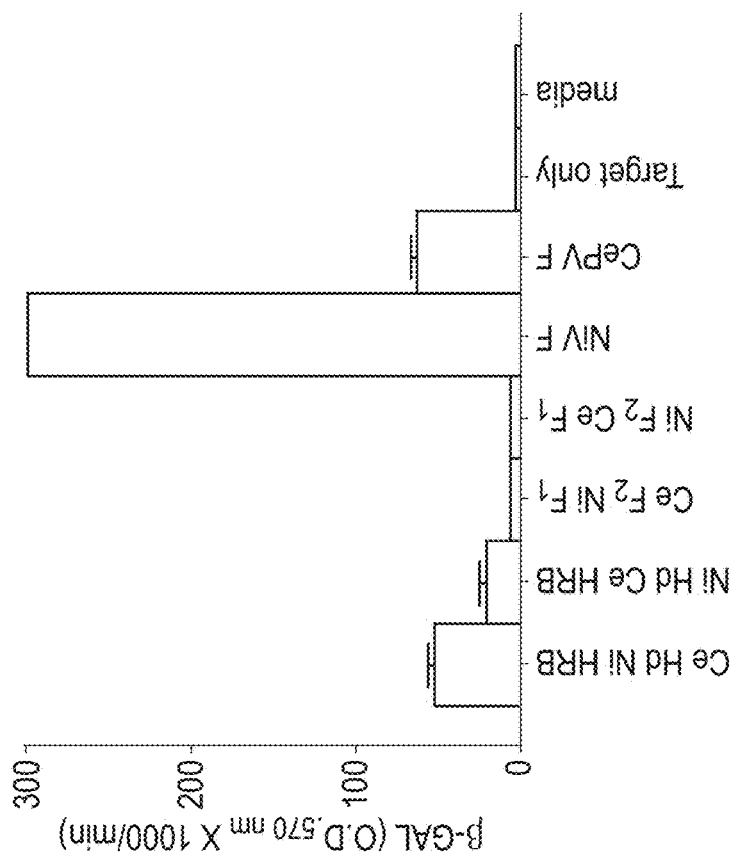
FIG. 6A
FIG. 6B

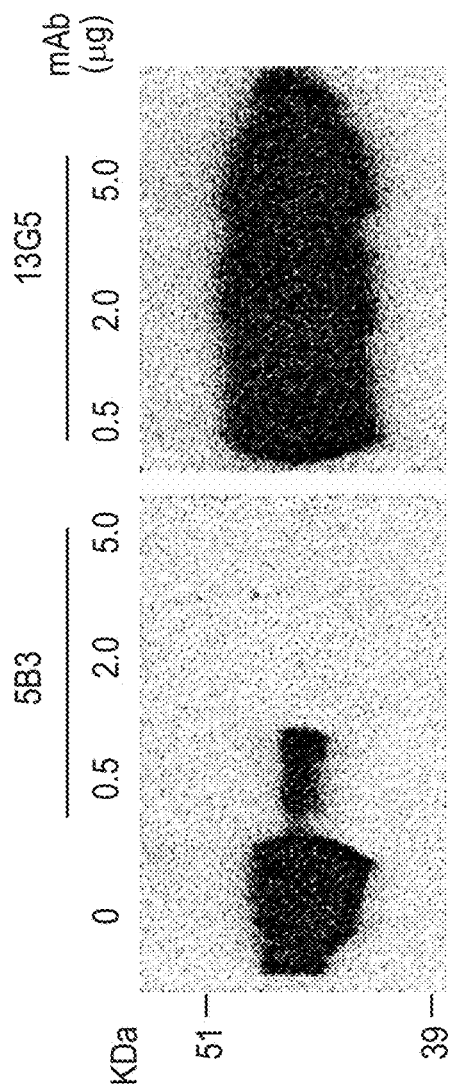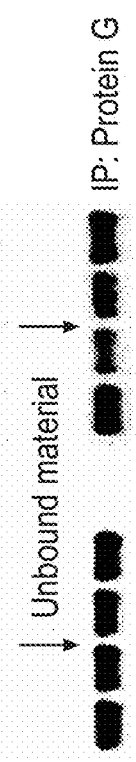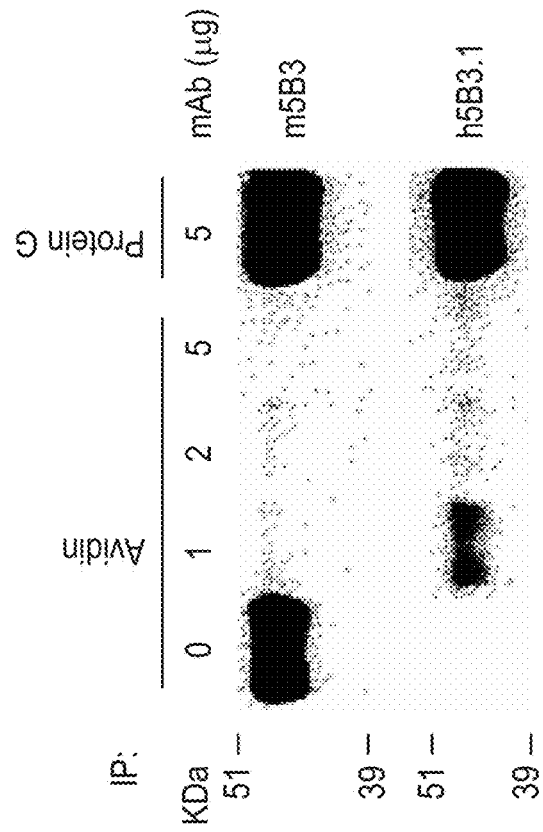
FIG. 8A
FIG. 8B
FIG. 8C

SEQUENCE LISTING

```
<160> NUMBER OF SEQ ID NOS: 80

<210> SEQ ID NO 1
<211> LENGTH: 117
<212> TYPE: PRT
<213> ORGANISM: Artificial Sequence
<220> FEATURE:
<223> OTHER INFORMATION: Peptide

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Arg Leu Glu Trp Val
        35                  40                  45

Ala Met Ile Ser Ser Gly Gly Ser Tyr Ser Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Gly Asp Tyr Ala Trp Phe Ala Tyr Trp Gly Gln Gly Thr
            100                 105                 110

Leu Val Thr Val Ser
        115

<210> SEQ ID NO 2
<211> LENGTH: 25
<212> TYPE: PRT
<213> ORGANISM: Artificial Sequence
<220> FEATURE:
<223> OTHER INFORMATION: Peptide

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Ser
            20                  25
```

<210> SEQ ID NO 3
<211> LENGTH: 10
<212> TYPE: PRT
<213> ORGANISM: Artificial Sequence
<220> FEATURE:
<223> OTHER INFORMATION: Peptide

<400> SEQUENCE: 3

Gly Phe Thr Phe Ser Ser Tyr Asp Met Ser
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide

<400> SEQUENCE: 4

Trp Val Arg Gln Thr Pro Glu Lys Arg Leu Glu Trp Val Ala
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Peptide

<400> SEQUENCE: 5

Met Ile Ser Ser Gly Gly Ser Tyr Ser Tyr Tyr Pro Asp Ser Val Lys
1               5                   10                  15

Gly

<210> SEQ ID NO 6
<211> LENGTH: 32
<212> TYPE: PRT
<213> ORGANISM: Artificial Sequence
<220> FEATURE:
<223> OTHER INFORMATION: Peptide

<400> SEQUENCE: 6

Arg Phe Thr Ile Ser Arg Asp Asn Ala Lys Asn Thr Leu Tyr Leu Gln
1               5                   10                  15

Met Ser Ser Leu Arg Ser Glu Asp Thr Ala Met Tyr Tyr Cys Ala Arg
                20                  25                  30

<210> SEQ ID NO 7
<211> LENGTH: 9
<212> TYPE: PRT
<213> ORGANISM: Artificial Sequence
<220> FEATURE:
<223> OTHER INFORMATION: Peptide

<400> SEQUENCE: 7

Gln Gly Asp Tyr Ala Trp Phe Ala Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Peptide

<400> SEQUENCE: 8

Trp Gly Gln Gly Thr Leu Val Thr Val Ser
1               5                   10

<210> SEQ ID NO 9
<211> LENGTH: 108
<212> TYPE: PRT
<213> ORGANISM: Artificial Sequence
<220> FEATURE:
<223> OTHER INFORMATION: Peptide

<400> SEQUENCE: 9

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Phe Tyr Ser Thr Pro Phe
                85                  90                  95

Thr Phe Gly Gly Gly Thr Lys Leu Glu Ile Lys Arg
            100                 105

<210> SEQ ID NO 10
<211> LENGTH: 23
<212> TYPE: PRT
<213> ORGANISM: Artificial Sequence
<220> FEATURE:
<223> OTHER INFORMATION: Peptide

<400> SEQUENCE: 10

Asp Ile Gln Met Thr Gln Ser Pro Ala Ser Gln Ser Ala Ser Leu Gly
1               5                   10                  15

Glu Ser Val Thr Ile Thr Cys
            20

<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Leu Ala Ser Gln Thr Ile Gly Thr Trp
1               5

<210> SEQ ID NO 12
<211> LENGTH: 17
<212> TYPE: PRT
<213> ORGANISM: Artificial Sequence
<220> FEATURE:
<223> OTHER INFORMATION: Peptide

<400> SEQUENCE: 12

Leu Ala Trp Tyr Gln Gln Lys Pro Gly Lys Ser Pro Gln Leu Leu Ile
1               5                   10                  15

Tyr

<210> SEQ ID NO 13
<211> LENGTH: 7
<212> TYPE: PRT
<213> ORGANISM: Artificial Sequence
<220> FEATURE:
<223> OTHER INFORMATION: Peptide

<400> SEQUENCE: 13

Ala Ala Thr Ser Leu Ala Asp
1               5

<210> SEQ ID NO 14
<211> LENGTH: 32
<212> TYPE: PRT
<213> ORGANISM: Artificial Sequence
<220> FEATURE:
<223> OTHER INFORMATION: Peptide

<400> SEQUENCE: 14

Gly Val Pro Ser Arg Phe Ser Gly Ser Gly Ser Gly Thr Lys Phe Ser
1               5                   10                  15

Phe Lys Ile Ser Ser Leu Gln Ala Glu Asp Phe Val Ser Tyr Tyr Cys
            20                  25                  30

<210> SEQ ID NO 15
<211> LENGTH: 9
<212> TYPE: PRT
<213> ORGANISM: Artificial Sequence
<220> FEATURE:
<223> OTHER INFORMATION: Peptide

<400> SEQUENCE: 15

Gln Gln Phe Tyr Ser Thr Pro Phe Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Peptide

<400> SEQUENCE: 16

Phe Gly Gly Gly Thr Lys Leu Glu Ile Lys Arg
1               5                   10

<210> SEQ ID NO 17
<211> LENGTH: 117
<212> TYPE: PRT
<213> ORGANISM: Artificial Sequence
<220> FEATURE:
<223> OTHER INFORMATION: Peptide

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Met Ile Ser Ser Gly Gly Ser Tyr Ser Tyr Tyr Pro Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95
Ala Arg Gln Gly Asp Tyr Ala Trp Phe Ala Tyr Trp Gly Gln Gly Thr
                        100                 105                 110
Leu Val Thr Val Ser
            115

<210> SEQ ID NO 18
<211> LENGTH: 25
<212> TYPE: PRT
<213> ORGANISM: Artificial Sequence
<220> FEATURE:
<223> OTHER INFORMATION: Peptide

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 19
<211> LENGTH: 10
<212> TYPE: PRT
<213> ORGANISM: Artificial Sequence
<220> FEATURE:
<223> OTHER INFORMATION: Peptide

<400> SEQUENCE: 19

Gly Phe Thr Phe Ser Ser Tyr Asp Met Ser
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Peptide

<400> SEQUENCE: 20

Trp Val Arg Gln Ala Pro Gly Lys Gly Leu Glu Trp Val Ala
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Peptide

<400> SEQUENCE: 21

Met Ile Ser Ser Gly Gly Ser Tyr Ser Tyr Tyr Pro Asp Ser Val Lys
1               5                   10                  15

Gly

<210> SEQ ID NO 22
<211> LENGTH: 32
<212> TYPE: PRT
<213> ORGANISM: Artificial Sequence
<220> FEATURE:
<223> OTHER INFORMATION: Peptide

<400> SEQUENCE: 22

Arg Phe Thr Ile Ser Arg Asp Asn Ser Lys Asn Thr Leu Tyr Leu Gln
```

```
                    1               5                   10                  15
Met Asn Ser Leu Arg Ala Glu Asp Thr Ala Val Tyr Tyr Cys Ala Arg
                        20                  25                  30
```

<210> SEQ ID NO 23
<211> LENGTH: 9
<212> TYPE: PRT
<213> ORGANISM: Artificial Sequence
<220> FEATURE:
<223> OTHER INFORMATION: Peptide

<400> SEQUENCE: 23

```
Gln Gly Asp Tyr Ala Trp Phe Ala Tyr
1               5
```

<210> SEQ ID NO 24
<211> LENGTH: 10
<212> TYPE: PRT
<213> ORGANISM: Artificial Sequence
<220> FEATURE:
<223> OTHER INFORMATION: Peptide

<400> SEQUENCE: 24

```
Trp Gly Gln Gly Thr Leu Val Thr Val Ser
1               5                   10
```

<210> SEQ ID NO 25
<211> LENGTH: 108
<212> TYPE: PRT
<213> ORGANISM: Artificial Sequence
<220> FEATURE:
<223> OTHER INFORMATION: Peptide

<400> SEQUENCE: 25

```
Asp Ile Gln Met Thr Gln Ser Pro Ser Ser Leu Ser Ala Ser Val Gly
1               5                   10                  15
Asp Arg Val Thr Ile Thr Cys Leu Ala Ser Gln Thr Ile Gly Thr Trp
                20                  25                  30
Leu Ala Trp Tyr Gln Gln Lys Pro Gly Lys Ala Pro Lys Leu Leu Ile
            35                  40                  45
Tyr Ala Ala Thr Ser Leu Ala Asp Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Tyr Ser Thr Pro Phe
                85                  90                  95
Thr Phe Gly Gly Gly Thr Lys Leu Glu Ile Lys Arg
                100                 105
```

<210> SEQ ID NO 26
<211> LENGTH: 23
<212> TYPE: PRT
<213> ORGANISM: Artificial Sequence
<220> FEATURE:
<223> OTHER INFORMATION: Peptide

<400> SEQUENCE: 26

```
Asp Ile Gln Met Thr Gln Ser Pro Ser Ser Leu Ser Ala Ser Val Gly
1               5                   10                  15
Asp Arg Val Thr Ile Thr Cys
                20
```

```
<210> SEQ ID NO 27
<211> LENGTH: 9
<212> TYPE: PRT
<213> ORGANISM: Artificial Sequence
<220> FEATURE:
<223> OTHER INFORMATION: Peptide

<400> SEQUENCE: 27

Leu Ala Ser Gln Thr Ile Gly Thr Trp
1               5

<210> SEQ ID NO 28
<211> LENGTH: 17
<212> TYPE: PRT
<213> ORGANISM: Artificial Sequence
<220> FEATURE:
<223> OTHER INFORMATION: Peptide

<400> SEQUENCE: 28

Leu Ala Trp Tyr Gln Gln Lys Pro Gly Lys Ala Pro Lys Leu Leu Ile
1               5                   10                  15

Tyr

<210> SEQ ID NO 29
<211> LENGTH: 7
<212> TYPE: PRT
<213> ORGANISM: Artificial Sequence
<220> FEATURE:
<223> OTHER INFORMATION: Peptide

<400> SEQUENCE: 29

Ala Ala Thr Ser Leu Ala Asp
1               5

<210> SEQ ID NO 30
<211> LENGTH: 32
<212> TYPE: PRT
<213> ORGANISM: Artificial Sequence
<220> FEATURE:
<223> OTHER INFORMATION: Peptide

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 31
<211> LENGTH: 9
<212> TYPE: PRT
<213> ORGANISM: Artificial Sequence
<220> FEATURE:
<223> OTHER INFORMATION: Peptide

<400> SEQUENCE: 31

Gln Gln Phe Tyr Ser Thr Pro Phe Thr
1               5

<210> SEQ ID NO 32
<211> LENGTH: 11
<212> TYPE: PRT
<213> ORGANISM: Artificial Sequence
<220> FEATURE:
<223> OTHER INFORMATION: Peptide

<400> SEQUENCE: 32
```

```
Phe Gly Gly Gly Thr Lys Leu Glu Ile Lys Arg
1               5                   10
```

<210> SEQ ID NO 33
<211> LENGTH: 117
<212> TYPE: PRT
<213> ORGANISM: Artificial Sequence
<220> FEATURE:
<223> OTHER INFORMATION: Peptide

<400> SEQUENCE: 33

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ala Met Ile Ser Ser Gly Gly Ser Tyr Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Ala Trp Phe Asp Ile Trp Gly Gln Gly Thr
            100                 105                 110

Leu Val Thr Val Ser
        115
```

<210> SEQ ID NO 34
<211> LENGTH: 25
<212> TYPE: PRT
<213> ORGANISM: Artificial Sequence
<220> FEATURE:
<223> OTHER INFORMATION: Peptide

<400> SEQUENCE: 34

```
Glu Val Gln Leu Val Glu Ser Gly Gly Gly Leu Val Lys Pro Gly Gly
1               5                   10                  15

Ser Leu Arg Leu Ser Cys Ala Ala Ser
            20                  25
```

<210> SEQ ID NO 35
<211> LENGTH: 10
<212> TYPE: PRT
<213> ORGANISM: Artificial Sequence
<220> FEATURE:
<223> OTHER INFORMATION: Peptide

<400> SEQUENCE: 35

```
Gly Phe Thr Phe Ser Ser Tyr Ser Met Ser
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: Peptide

<400> SEQUENCE: 36

```
Trp Val Arg Gln Ala Pro Gly Lys Gly Leu Glu Trp Val Ala
1               5                   10
```

```
<210> SEQ ID NO 37
<211> LENGTH: 17
<212> TYPE: PRT
<213> ORGANISM: Artificial Sequence
<220> FEATURE:
<223> OTHER INFORMATION: Peptide

<400> SEQUENCE: 37

Met Ile Ser Ser Gly Gly Ser Tyr Ser Tyr Tyr Ala Asp Ser Val Lys
1               5                   10                  15

Gly

<210> SEQ ID NO 38
<211> LENGTH: 32
<212> TYPE: PRT
<213> ORGANISM: Artificial Sequence
<220> FEATURE:
<223> OTHER INFORMATION: Peptide

<400> SEQUENCE: 38

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 39
<211> LENGTH: 9
<212> TYPE: PRT
<213> ORGANISM: Artificial Sequence
<220> FEATURE:
<223> OTHER INFORMATION: Peptide

<400> SEQUENCE: 39

Gln Gly Asp Tyr Ala Trp Phe Asp Ile
1               5

<210> SEQ ID NO 40
<211> LENGTH: 10
<212> TYPE: PRT
<213> ORGANISM: Artificial Sequence
<220> FEATURE:
<223> OTHER INFORMATION: Peptide

<400> SEQUENCE: 40

Trp Gly Gln Gly Thr Leu Val Thr Val Ser
1               5                   10

<210> SEQ ID NO 41
<211> LENGTH: 108
<212> TYPE: PRT
<213> ORGANISM: Artificial Sequence
<220> FEATURE:
<223> OTHER INFORMATION: Peptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Ser Thr Pro Phe
                 85                  90                  95

Thr Phe Gly Gly Gly Thr Lys Leu Glu Ile Lys Arg
            100                 105

<210> SEQ ID NO 42
<211> LENGTH: 23
<212> TYPE: PRT
<213> ORGANISM: Artificial Sequence
<220> FEATURE:
<223> OTHER INFORMATION: Peptide

<400> SEQUENCE: 42

Asp Ile Gln Met Thr Gln Ser Pro Ser Ser Leu Ser Ala Ser Val Gly
 1               5                  10                  15

Asp Arg Val Thr Ile Thr Cys
                 20

<210> SEQ ID NO 43
<211> LENGTH: 9
<212> TYPE: PRT
<213> ORGANISM: Artificial Sequence
<220> FEATURE:
<223> OTHER INFORMATION: Peptide

<400> SEQUENCE: 43

Leu Ala Ser Gln Thr Ile Gly Thr Trp
 1               5

<210> SEQ ID NO 44
<211> LENGTH: 17
<212> TYPE: PRT
<213> ORGANISM: Artificial Sequence
<220> FEATURE:
<223> OTHER INFORMATION: Peptide

<400> SEQUENCE: 44

Leu Ala Trp Tyr Gln Gln Lys Pro Gly Lys Ala Pro Lys Leu Leu Ile
 1               5                  10                  15

Tyr

<210> SEQ ID NO 45
<211> LENGTH: 7
<212> TYPE: PRT
<213> ORGANISM: Artificial Sequence
<220> FEATURE:
<223> OTHER INFORMATION: Peptide

<400> SEQUENCE: 45

Ala Ala Thr Ser Leu Ala Asp
 1               5

<210> SEQ ID NO 46
<211> LENGTH: 32
<212> TYPE: PRT
<213> ORGANISM: Artificial Sequence
<220> FEATURE:
<223> OTHER INFORMATION: Peptide

<400> SEQUENCE: 46

Gly Val Pro Ser Arg Phe Ser Gly Ser Gly Ser Gly Thr Asp Phe Thr
 1               5                  10                  15
```

Leu Thr Ile Ser Ser Leu Gln Pro Glu Asp Phe Ala Thr Tyr Tyr Cys
                20                  25                  30

<210> SEQ ID NO 47
<211> LENGTH: 9
<212> TYPE: PRT
<213> ORGANISM: Artificial Sequence
<220> FEATURE:
<223> OTHER INFORMATION: Peptide

<400> SEQUENCE: 47

Gln Gln Phe Tyr Ser Thr Pro Phe Thr
1               5

<210> SEQ ID NO 48
<211> LENGTH: 11
<212> TYPE: PRT
<213> ORGANISM: Artificial Sequence
<220> FEATURE:
<223> OTHER INFORMATION: Peptide

<400> SEQUENCE: 48

Phe Gly Gly Gly Thr Lys Leu Glu Ile Lys Arg
1               5                   10

<210> SEQ ID NO 49
<211> LENGTH: 240
<212> TYPE: PRT
<213> ORGANISM: Artificial Sequence
<220> FEATURE:
<223> OTHER INFORMATION: Peptide

<400> SEQUENCE: 49

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Asp Met Ser Trp Val Arg Gln Thr Pro Glu Lys Arg Leu Glu Trp Val
            35                  40                  45

Ala Met Ile Ser Ser Gly Gly Ser Tyr Ser Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Gly Asp Tyr Ala Trp Phe Ala Tyr Trp Gly Gln Gly Thr
            100                 105                 110

Leu Val Thr Val Ser Gly Gly Gly Gly Ser Gly Gly Gly Gly Ser Gly
        115                 120                 125

Gly Gly Ser Asp Ile Gln Met Thr Gln Ser Pro Ala Ser Gln Ser
    130                 135                 140

Ala Ser Leu Gly Glu Ser Val Thr Ile Thr Cys Leu Ala Ser Gln Thr
145                 150                 155                 160

Ile Gly Thr Trp Leu Ala Trp Tyr Gln Gln Lys Pro Gly Lys Ser Pro
                165                 170                 175

Gln Leu Leu Ile Tyr Ala Ala Thr Ser Leu Ala Asp Gly Val Pro Ser
            180                 185                 190

Arg Phe Ser Gly Ser Gly Ser Gly Thr Lys Phe Ser Phe Lys Ile Ser
        195                 200                 205

Ser Leu Gln Ala Glu Asp Phe Val Ser Tyr Tyr Cys Gln Gln Phe Tyr

```
Ser Thr Pro Phe Thr Phe Gly Gly Gly Thr Lys Leu Glu Ile Lys Arg
225                 230                 235                 240
```

<210> SEQ ID NO 50
<211> LENGTH: 240
<212> TYPE: PRT
<213> ORGANISM: Artificial Sequence
<220> FEATURE:
<223> OTHER INFORMATION: Peptide

<400> SEQUENCE: 50

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Met Ile Ser Ser Gly Gly Ser Tyr Ser Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Tyr Ala Trp Phe Ala Tyr Trp Gly Gln Gly Thr
            100                 105                 110

Leu Val Thr Val Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Leu Ala Ser Gln Thr
145                 150                 155                 160

Ile Gly Thr Trp Leu Ala Trp Tyr Gln Gln Lys Pro Gly Lys Ala Pro
                165                 170                 175

Lys Leu Leu Ile Tyr Ala Ala Thr Ser Leu Ala Asp Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Phe Tyr
    210                 215                 220

Ser Thr Pro Phe Thr Phe Gly Gly Gly Thr Lys Leu Glu Ile Lys Arg
225                 230                 235                 240
```

<210> SEQ ID NO 51
<211> LENGTH: 240
<212> TYPE: PRT
<213> ORGANISM: Artificial Sequence
<220> FEATURE:
<223> OTHER INFORMATION: Peptide

<400> SEQUENCE: 51

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45
```

```
Ala Met Ile Ser Ser Gly Gly Ser Tyr Ser Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Asp Tyr Ala Trp Phe Asp Ile Trp Gly Gln Gly Thr
            100                 105                 110

Leu Val Thr Val Ser Gly Gly Gly Ser Gly Gly Gly Gly Ser Gly
            115                 120                 125

Gly Gly Gly Ser Asp Ile Gln Met Thr Gln Ser Pro Ser Ser Leu Ser
130                 135                 140

Ala Ser Val Gly Asp Arg Val Thr Ile Thr Cys Leu Ala Ser Gln Thr
145                 150                 155                 160

Ile Gly Thr Trp Leu Ala Trp Tyr Gln Gln Lys Pro Gly Lys Ala Pro
                165                 170                 175

Lys Leu Leu Ile Tyr Ala Ala Ser Leu Ala Asp Gly Val Pro Ser
            180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Phe Tyr
210                 215                 220

Ser Thr Pro Phe Thr Phe Gly Gly Gly Thr Lys Leu Glu Ile Lys Arg
225                 230                 235                 240

<210> SEQ ID NO 52
<211> LENGTH: 15
<212> TYPE: PRT
<213> ORGANISM: Artificial Sequence
<220> FEATURE:
<223> OTHER INFORMATION: Peptide

<400> SEQUENCE: 52

Gly Gly Gly Gly Ser Gly Gly Gly Ser Gly Gly Gly Ser
 1               5                  10                  15

<210> SEQ ID NO 53
<211> LENGTH: 81
<212> TYPE: PRT
<213> ORGANISM: Artificial Sequence
<220> FEATURE:
<223> OTHER INFORMATION: Peptide

<400> SEQUENCE: 53

Glu Val Gln Leu Val Glu Ser Gly Gly Gly Leu Val Lys Pro Gly Gly
 1               5                  10                  15

Ser Leu Arg Leu Ser Cys Ala Ala Ser Trp Val Arg Gln Ala Pro Gly
             20                  25                  30

Lys Gly Leu Glu Trp Val Ala Arg Phe Thr Ile Ser Arg Asp Asn Ser
         35                  40                  45

Lys Asn Thr Leu Tyr Leu Gln Met Asn Ser Leu Arg Ala Glu Asp Thr
     50                  55                  60

Ala Val Tyr Tyr Cys Ala Arg Trp Gly Gln Gly Thr Leu Val Thr Val
 65                  70                  75                  80

Ser

<210> SEQ ID NO 54
<211> LENGTH: 81
```

```
<212> TYPE: PRT
<213> ORGANISM: Artificial Sequence
<220> FEATURE:
<223> OTHER INFORMATION: Peptide

<400> SEQUENCE: 54

Glu Val Gln Leu Val Glu Ser Gly Gly Gly Leu Val Lys Pro Gly Gly
1               5                   10                  15

Ser Leu Lys Leu Ser Cys Ala Ala Ser Trp Val Arg Gln Thr Pro Glu
            20                  25                  30

Lys Arg Leu Glu Trp Val Ala Arg Phe Thr Ile Ser Arg Asp Asn Ala
        35                  40                  45

Lys Asn Thr Leu Tyr Leu Gln Met Ser Ser Leu Arg Ser Glu Asp Thr
    50                  55                  60

Ala Met Tyr Tyr Cys Ala Arg Trp Gly Gln Gly Thr Leu Val Thr Val
65                  70                  75                  80

Ser

<210> SEQ ID NO 55
<211> LENGTH: 81
<212> TYPE: PRT
<213> ORGANISM: Artificial Sequence
<220> FEATURE:
<223> OTHER INFORMATION: Peptide

<400> SEQUENCE: 55

Glu Val Gln Leu Val Glu Ser Gly Gly Gly Leu Ala Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ser
        35                  40                  45

Lys Asn Thr Ala Tyr Leu Gln Met Asn Ser Leu Lys Ser Asp Asp Pro
    50                  55                  60

Ala Val Tyr Tyr Cys Thr Arg Trp Gly Gln Gly Thr Leu Val Thr Val
65                  70                  75                  80

Ser

<210> SEQ ID NO 56
<211> LENGTH: 81
<212> TYPE: PRT
<213> ORGANISM: Artificial Sequence
<220> FEATURE:
<223> OTHER INFORMATION: Peptide

<400> SEQUENCE: 56

Glu Val Gln Leu Val Glu Ser Gly Gly Gly Leu Val Lys Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Gly Arg Phe Thr Ile Ser Arg Asp Asp Ser
        35                  40                  45

Lys Ser Ile Ala Tyr Leu Gln Met Asn Ser Leu Arg Thr Glu Asp Thr
    50                  55                  60

Ala Val Tyr Tyr Cys Thr Arg Trp Gly Gln Gly Thr Leu Val Thr Val
65                  70                  75                  80

Ser
```

```
<210> SEQ ID NO 57
<211> LENGTH: 81
<212> TYPE: PRT
<213> ORGANISM: Artificial Sequence
<220> FEATURE:
<223> OTHER INFORMATION: Peptide

<400> SEQUENCE: 57
```

Glu Val Gln Leu Val Glu Ser Gly Gly Gly Val Val Gln Pro Gly Arg
1               5                   10                  15

Ser Leu Arg Leu Ser Cys Ala Ala Ser Trp Val Arg Gln Ala Pro Gly
            20                  25                  30

Lys Gly Leu Glu Trp Val Ala Arg Phe Ser Ile Ser Arg Asp Asn Ala
        35                  40                  45

Arg Asn Ser Leu Tyr Leu Gln Met Asn Ser Leu Arg Asp Asp Asp Thr
    50                  55                  60

Ser Val Tyr Tyr Cys Val Arg Trp Gly Gln Gly Thr Leu Val Thr Val
65                  70                  75                  80

Ser

```
<210> SEQ ID NO 58
<211> LENGTH: 81
<212> TYPE: PRT
<213> ORGANISM: Artificial Sequence
<220> FEATURE:
<223> OTHER INFORMATION: Peptide

<400> SEQUENCE: 58
```

Glu Val Gln Leu Val Glu Ser Gly Gly Gly Pro Gly Gln Ala Trp Gly
1               5                   10                  15

Val Leu Arg Leu Ser Cys Ala Ala Ser Trp Val Arg Gln Ala Pro Gly
            20                  25                  30

Lys Gly Leu Glu Trp Val Ser Arg Phe Thr Ile Ser Arg Asp Asn Ala
        35                  40                  45

Lys Asn Ser Leu Tyr Leu Gln Met Asn Ser Leu Arg Ala Asp Asp Thr
    50                  55                  60

Ala Val Tyr Tyr Cys Ala Arg Trp Gly Arg Gly Thr Leu Val Thr Val
65                  70                  75                  80

Ser

```
<210> SEQ ID NO 59
<211> LENGTH: 81
<212> TYPE: PRT
<213> ORGANISM: Artificial Sequence
<220> FEATURE:
<223> OTHER INFORMATION: Peptide

<400> SEQUENCE: 59
```

Glu Val Gln Leu Val Glu Ser Gly Ala Glu Val Lys Lys Pro Gly Glu
1               5                   10                  15

Ser Leu Lys Ile Ser Cys Lys Gly Ser Trp Val Arg Gln Met Pro Gly
            20                  25                  30

Lys Gly Leu Glu Trp Met Gly Gln Val Thr Ile Ser Ala Asp Lys Ser
        35                  40                  45

Ile Thr Thr Ala Tyr Leu Gln Trp Ser Ser Leu Lys Ala Ser Asp Thr
    50                  55                  60

Ala Met Tyr Tyr Cys Ala Arg Trp Gly Gln Gly Thr Pro Val Thr Val
65                  70                  75                  80

Ser

<210> SEQ ID NO 60
<211> LENGTH: 81
<212> TYPE: PRT
<213> ORGANISM: Artificial Sequence
<220> FEATURE:
<223> OTHER INFORMATION: Peptide

<400> SEQUENCE: 60

Glu Val Gln Leu Val Glu Ser Gly Gly Gly Val Val Gln Pro Gly Arg
1               5                   10                  15

Ser Leu Arg Leu Ser Cys Ala Ala Ser Trp Val Arg Gln Ala Pro Gly
                20                  25                  30

Lys Gly Leu Glu Trp Val Ala Arg Phe Thr Ile Ser Arg Asp Asn Ser
            35                  40                  45

Lys Asn Thr Leu Tyr Leu Gln Met Asn Ser Leu Arg Ala Glu Asp Thr
50                  55                  60

Ala Val Tyr Tyr Cys Ala Arg Trp Gly Gln Gly Thr Leu Val Thr Val
65                  70                  75                  80

Ser

<210> SEQ ID NO 61
<211> LENGTH: 81
<212> TYPE: PRT
<213> ORGANISM: Artificial Sequence
<220> FEATURE:
<223> OTHER INFORMATION: Peptide

<400> SEQUENCE: 61

Glu Val Gln Leu Val Glu Ser Gly Ala Glu Val Lys Arg Pro Gly Ala
1               5                   10                  15

Ser Val Lys Val Ser Cys Lys Ala Ser Trp Val Arg Gln Ala Pro Gly
                20                  25                  30

Gln Gly Leu Glu Trp Met Gly Arg Val Thr Met Thr Thr Glu Thr Ser
            35                  40                  45

Thr Ser Thr Ala Tyr Met Glu Leu Arg Ser Leu Arg Ser Asp Asp Thr
50                  55                  60

Ala Val Tyr Tyr Cys Ala Arg Trp Gly Gln Gly Thr Leu Val Thr Val
65                  70                  75                  80

Ser

<210> SEQ ID NO 62
<211> LENGTH: 81
<212> TYPE: PRT
<213> ORGANISM: Artificial Sequence
<220> FEATURE:
<223> OTHER INFORMATION: Peptide

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
                20                  25                  30

Lys Gly Leu Glu Trp Val Ser Arg Phe Thr Ile Ser Arg Asp Asn Ser
            35                  40                  45

Lys Asn Thr Leu Phe Leu Gln Met Asn Ser Leu Arg Ala Glu Asp Thr
50                  55                  60

Ala Val Tyr Tyr Cys Ala Arg Trp Gly Gln Gly Thr Leu Val Thr Val
65                  70                  75                  80

Ser

<210> SEQ ID NO 63
<211> LENGTH: 81
<212> TYPE: PRT
<213> ORGANISM: Artificial Sequence
<220> FEATURE:
<223> OTHER INFORMATION: Peptide

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Ala Arg Phe Ser Ile Ser Arg Asp Asn Ala
        35                  40                  45

Arg Asn Ser Leu Tyr Leu Gln Met Asn Ser Leu Arg Asp Asp Asp Thr
    50                  55                  60

Ser Val Tyr Tyr Cys Val Arg Trp Gly Gln Gly Thr Leu Val Thr Val
65                  70                  75                  80

Ser
```

<210> SEQ ID NO 64
<211> LENGTH: 81
<212> TYPE: PRT
<213> ORGANISM: Artificial Sequence
<220> FEATURE:
<223> OTHER INFORMATION: Peptide

<400> SEQUENCE: 64

```
Glu Val Gln Leu Val Glu Ser Gly Gly Gly Val Val Gln Pro Gly Arg
1               5                   10                  15

Ser Leu Arg Leu Ser Cys Ala Ala Ser Trp Val Arg Gln Ala Pro Gly
            20                  25                  30

Lys Gly Leu Glu Trp Val Ala Arg Phe Thr Ile Ser Arg Asp Asn Ser
        35                  40                  45

Lys Asn Thr Leu Tyr Leu Gln Met Asn Ser Pro Arg Ala Glu Asp Thr
    50                  55                  60

Ala Val Tyr Tyr Cys Ala Arg Trp Gly Gln Gly Thr Leu Val Thr Val
65                  70                  75                  80

Ser
```

<210> SEQ ID NO 65
<211> LENGTH: 81
<212> TYPE: PRT
<213> ORGANISM: Artificial Sequence
<220> FEATURE:
<223> OTHER INFORMATION: Peptide

<400> SEQUENCE: 65

```
Glu Val Gln Leu Val Glu Ser Gly Gly Gly Leu Val Gln Pro Gly Gly
1               5                   10                  15

Ser Leu Arg Leu Thr Cys Ala Ala Ser Trp Val Arg Gln Ala Pro Gly
            20                  25                  30

Lys Gly Leu Glu Trp Val Ser Arg Phe Thr Ile Ser Arg Asp Asn Ser
        35                  40                  45

Glu Asn Met Leu Tyr Leu Gln Met Asn Ser Leu Arg Ala Glu Asp Thr
    50                  55                  60
```

```
Ala Val Tyr Tyr Cys Ala Arg Trp Gly Gln Gly Thr Leu Val Thr Val
 65                  70                  75                  80

Ser

<210> SEQ ID NO 66
<211> LENGTH: 81
<212> TYPE: PRT
<213> ORGANISM: Artificial Sequence
<220> FEATURE:
<223> OTHER INFORMATION: Peptide

<400> SEQUENCE: 66

Glu Val Gln Leu Val Glu Ser Gly Gly Gly Leu Val Lys Pro Gly Gly
  1               5                  10                  15

Ser Leu Arg Leu Ser Cys Ala Ala Ser Trp Val Arg Gln Ala Pro Gly
                 20                  25                  30

Lys Gly Leu Glu Trp Val Ser Arg Phe Thr Ile Ser Arg Asp Asn Ala
             35                  40                  45

Lys Asn Ser Leu Tyr Leu Gln Met Asn Ser Leu Arg Ala Glu Asp Thr
 50                  55                  60

Ala Val Tyr Tyr Cys Ala Arg Trp Gly Gln Gly Thr Leu Val Thr Val
 65                  70                  75                  80

Ser

<210> SEQ ID NO 67
<211> LENGTH: 83
<212> TYPE: PRT
<213> ORGANISM: Artificial Sequence
<220> FEATURE:
<223> OTHER INFORMATION: Peptide

<400> SEQUENCE: 67

Asp Ile Gln Met Thr Gln Ser Pro Ser Ser Leu Ser Ala Ser Val Gly
  1               5                  10                  15

Asp Arg Val Thr Ile Thr Cys Leu Ala Trp Tyr Gln Gln Lys Pro Gly
                 20                  25                  30

Lys Ala Pro Lys Leu Leu Ile Tyr Gly Val Pro Ser Arg Phe Ser Gly
             35                  40                  45

Ser Gly Ser Gly Thr Asp Phe Thr Leu Thr Ile Ser Ser Leu Gln Pro
 50                  55                  60

Glu Asp Phe Ala Thr Tyr Tyr Cys Thr Phe Gly Gly Gly Thr Lys Leu
 65                  70                  75                  80

Glu Ile Lys

<210> SEQ ID NO 68
<211> LENGTH: 83
<212> TYPE: PRT
<213> ORGANISM: Artificial Sequence
<220> FEATURE:
<223> OTHER INFORMATION: Peptide

<400> SEQUENCE: 68

Asp Ile Gln Met Thr Gln Ser Pro Ala Ser Gln Ser Ala Ser Leu Gly
  1               5                  10                  15

Glu Ser Val Thr Ile Thr Cys Leu Ala Trp Tyr Gln Gln Lys Pro Gly
                 20                  25                  30

Lys Ser Pro Gln Leu Leu Ile Tyr Gly Val Pro Ser Arg Phe Ser Gly
             35                  40                  45

Ser Gly Ser Gly Thr Lys Phe Ser Phe Lys Ile Ser Ser Leu Gln Ala
```

```
                     50                  55                  60
Glu Asp Phe Val Ser Tyr Tyr Cys Thr Phe Gly Gly Gly Thr Lys Leu
 65                  70                  75                  80

Glu Ile Lys

<210> SEQ ID NO 69
<211> LENGTH: 83
<212> TYPE: PRT
<213> ORGANISM: Artificial Sequence
<220> FEATURE:
<223> OTHER INFORMATION: Peptide

<400> SEQUENCE: 69

Asp Ile Gln Met Thr Gln Ser Pro Ser Ser Leu Ser Ala Ser Val Gly
 1               5                  10                  15

Asp Arg Val Thr Ile Thr Cys Leu Asn Trp Tyr Gln Gln Lys Pro Gly
                20                  25                  30

Lys Ala Pro Lys Leu Leu Ile Tyr Gly Val Pro Ser Arg Phe Ser Gly
            35                  40                  45

Ser Gly Ser Gly Thr Glu Phe Thr Leu Thr Ile Ser Ser Leu Gln Pro
        50                  55                  60

Asp Asp Phe Ala Thr Tyr Tyr Cys Thr Phe Gly Gln Gly Thr Lys Leu
 65                  70                  75                  80

Glu Ile Lys

<210> SEQ ID NO 70
<211> LENGTH: 83
<212> TYPE: PRT
<213> ORGANISM: Artificial Sequence
<220> FEATURE:
<223> OTHER INFORMATION: Peptide

<400> SEQUENCE: 70

Asp Ile Gln Met Thr Gln Ser Pro Ser Phe Leu Ser Ala Ser Val Gly
 1               5                  10                  15

Asp Arg Val Thr Ile Thr Cys Leu Ala Trp Tyr Gln Gln Lys Pro Gly
                20                  25                  30

Lys Ala Pro Lys Leu Leu Ile Tyr Gly Val Pro Ser Arg Phe Ser Gly
            35                  40                  45

Ser Gly Ser Gly Thr Asp Phe Thr Leu Thr Ile Ser Ser Leu Gln Pro
        50                  55                  60

Asp Asp Phe Ala Thr Tyr Tyr Cys Thr Phe Gly Gln Gly Thr Lys Leu
 65                  70                  75                  80

Glu Ile Lys

<210> SEQ ID NO 71
<211> LENGTH: 83
<212> TYPE: PRT
<213> ORGANISM: Artificial Sequence
<220> FEATURE:
<223> OTHER INFORMATION: Peptide

<400> SEQUENCE: 71

Asp Ile Gln Met Thr Gln Ser Pro Ser Thr Leu Ser Ala Ser Val Arg
 1               5                  10                  15

Asp Arg Val Thr Ile Thr Cys Leu Ala Trp Tyr Gln Gln Arg Pro Gly
                20                  25                  30

Lys Ala Pro Lys Leu Leu Ile Tyr Gly Val Pro Ser Arg Phe Ser Gly
            35                  40                  45
```

```
Ser Gly Ser Gly Ser Asp Phe Thr Leu Thr Ile Ser Ser Leu Gln Pro
        50                  55                  60

Glu Asp Phe Ala Thr Tyr Tyr Cys Thr Phe Gly Gly Gly Thr Lys Leu
65                  70                  75                  80

Glu Ile Lys

<210> SEQ ID NO 72
<211> LENGTH: 83
<212> TYPE: PRT
<213> ORGANISM: Artificial Sequence
<220> FEATURE:
<223> OTHER INFORMATION: Peptide

<400> SEQUENCE: 72

Asp Ile Gln Met Thr Gln Ser Pro Ser Ser Phe Ser Ala Ser Thr Gly
1               5                   10                  15

Asp Arg Val Thr Ile Thr Cys Leu Asn Trp Tyr Gln Gln Lys Pro Gly
            20                  25                  30

Lys Ala Pro Lys Leu Leu Ile Tyr Gly Val Pro Ser Arg Phe Ser Gly
        35                  40                  45

Ser Gly Ser Gly Thr Asp Phe Thr Leu Thr Ile Ser Ser Leu Gln Pro
        50                  55                  60

Glu Asp Phe Ala Thr Tyr Tyr Cys Gly Phe Gly Gly Gly Thr Lys Leu
65                  70                  75                  80

Glu Ile Lys

<210> SEQ ID NO 73
<211> LENGTH: 83
<212> TYPE: PRT
<213> ORGANISM: Artificial Sequence
<220> FEATURE:
<223> OTHER INFORMATION: Peptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Leu Ala Trp Tyr Gln Gln Lys Pro Gly
            20                  25                  30

Lys Ala Pro Lys Leu Leu Ile Tyr Gly Val Pro Ser Arg Phe Ser Gly
        35                  40                  45

Ser Gly Ser Gly Thr Glu Phe Thr Leu Thr Ile Ser Ser Leu Gln Pro
        50                  55                  60

Glu Asp Phe Ala Thr Tyr Tyr Cys Thr Phe Gly Gly Gly Thr Lys Leu
65                  70                  75                  80

Glu Ile Lys

<210> SEQ ID NO 74
<211> LENGTH: 83
<212> TYPE: PRT
<213> ORGANISM: Artificial Sequence
<220> FEATURE:
<223> OTHER INFORMATION: Peptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Leu Ala Trp Tyr Gln Gln Lys Pro Gly
            20                  25                  30
```

```
Lys Ala Pro Lys Leu Leu Ile Tyr Gly Val Pro Ser Arg Phe Ser Gly
            35                  40                  45

Ser Gly Ser Gly Thr Asp Phe Ala Leu Thr Ile Ser Ser Leu Gln Pro
        50                  55                  60

Glu Asp Phe Ala Thr Tyr Tyr Cys Thr Phe Gly Gln Gly Thr Lys Leu
65                  70                  75                  80

Glu Ile Lys
```

<210> SEQ ID NO 75
<211> LENGTH: 83
<212> TYPE: PRT
<213> ORGANISM: Artificial Sequence
<220> FEATURE:
<223> OTHER INFORMATION: Peptide

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Leu Ala Trp Tyr Gln Gln Lys Pro Gly
            20                  25                  30

Lys Ala Pro Lys Leu Leu Ile Tyr Gly Val Pro Ser Arg Phe Ser Gly
            35                  40                  45

Ser Gly Ser Gly Thr Glu Phe Thr Leu Thr Ile Ser Ser Leu Gln Pro
        50                  55                  60

Glu Asp Phe Ala Thr Tyr Tyr Cys Thr Phe Gly Gly Gly Thr Lys Leu
65                  70                  75                  80

Glu Ile Lys
```

<210> SEQ ID NO 76
<211> LENGTH: 83
<212> TYPE: PRT
<213> ORGANISM: Artificial Sequence
<220> FEATURE:
<223> OTHER INFORMATION: Peptide

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Leu Asn Trp Tyr Gln Gln Lys Pro Gly
            20                  25                  30

Lys Ala Pro Lys Leu Leu Ile Tyr Gly Val Pro Ser Arg Phe Ser Gly
            35                  40                  45

Ser Gly Ser Gly Thr Asp Phe Thr Leu Thr Ile Ser Ser Leu Gln Pro
        50                  55                  60

Glu Asp Phe Ala Ala Tyr Phe Cys Thr Phe Gly Gly Gly Thr Lys Leu
65                  70                  75                  80

Glu Ile Lys
```

<210> SEQ ID NO 77
<211> LENGTH: 83
<212> TYPE: PRT
<213> ORGANISM: Artificial Sequence
<220> FEATURE:
<223> OTHER INFORMATION: Peptide

<400> SEQUENCE: 77

```
Asp Ile Gln Met Thr Gln Ser Pro Ser Ser Leu Ser Ala Ser Val Gly
1               5                   10                  15

Asp Arg Val Thr Ile Thr Cys Leu Asn Trp Tyr Gln Gln Lys Pro Gly
```

```
                    20                  25                  30

Lys Ala Pro Lys Leu Leu Ile Tyr Gly Val Pro Ser Arg Phe Ser Gly
                35                  40                  45

Ser Gly Ser Gly Thr Asp Phe Thr Leu Thr Ile Ser Ser Leu Gln Pro
        50                  55                  60

Asp Asp Phe Ala Thr Tyr Tyr Cys Thr Phe Gly Gln Gly Thr Lys Leu
65                  70                  75                  80

Glu Ile Lys

<210> SEQ ID NO 78
<211> LENGTH: 83
<212> TYPE: PRT
<213> ORGANISM: Artificial Sequence
<220> FEATURE:
<223> OTHER INFORMATION: Peptide

<400> SEQUENCE: 78

Asp Ile Gln Met Thr Gln Ser Pro Ser Ser Leu Ser Ala Ser Ile Gly
1               5                   10                  15

Asp Arg Val Thr Ile Thr Cys Leu Ala Trp Tyr Gln Gln Lys Pro Gly
                20                  25                  30

Lys Ala Pro Lys Leu Leu Ile Tyr Gly Val Pro Ser Arg Phe Ser Gly
                35                  40                  45

Ser Gly Ser Gly Thr Asp Phe Thr Leu Thr Ile Ser Ser Leu Gln Pro
        50                  55                  60

Glu Asp Phe Ala Thr Tyr Tyr Cys Thr Phe Gly Arg Gly Thr Lys Leu
65                  70                  75                  80

Glu Ile Lys

<210> SEQ ID NO 79
<211> LENGTH: 83
<212> TYPE: PRT
<213> ORGANISM: Artificial Sequence
<220> FEATURE:
<223> OTHER INFORMATION: Peptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Leu Ala Trp Tyr Gln Gln Lys Pro Gly
                20                  25                  30

Lys Ala Pro Lys Leu Leu Ile Tyr Gly Val Pro Ser Arg Phe Ser Gly
                35                  40                  45

Ser Gly Ser Gly Thr Glu Phe Thr Leu Thr Ile Ser Ser Leu Gln Pro
        50                  55                  60

Glu Asp Phe Ala Thr Tyr Phe Cys Thr Phe Gly Gln Gly Thr Lys Leu
65                  70                  75                  80

Glu Ile Lys

<210> SEQ ID NO 80
<211> LENGTH: 83
<212> TYPE: PRT
<213> ORGANISM: Artificial Sequence
<220> FEATURE:
<223> OTHER INFORMATION: Peptide

<400> SEQUENCE: 80

Asp Ile Gln Met Thr Gln Ser Pro Ser Ser Leu Ser Ala Ser Val Gly
1               5                   10                  15
```

```
Asp Arg Val Thr Ile Thr Cys Leu Asn Trp Tyr Gln Gln Lys Pro Gly
            20              25              30

Lys Ala Pro Lys Leu Leu Ile Tyr Gly Val Pro Ser Arg Phe Ser Gly
        35              40              45

Ser Gly Ser Gly Thr Glu Phe Thr Leu Thr Ile Ser Ser Leu Gln Pro
    50              55              60

Glu Asp Phe Ala Thr Tyr Phe Cys Thr Phe Gly Gln Gly Thr Lys Leu
65              70              75              80

Glu Ile Lys
```

ANTIBODIES AGAINST F GLYCOPROTEIN OF HENDRA AND NIPAH VIRUSES

GOVERNMENT LICENSE RIGHTS

This invention was made with government support under AI077995 and AI054715 awarded by National Institutes of Health (NIH). The government has certain rights in the invention.

SEQUENCE LISTING SUBMISSION VIA EFS-WEB

A computer readable text file, entitled "044508-5048-01_SequenceListing.txt," created on or about Apr. 4, 2018, with a file size of about 46 KB contains the sequence listing for this application and is hereby incorporated by reference in its entirety.

FIELD OF THE INVENTION

This invention relates generally to the field of immunology and specifically to antibodies and antibody fragments that bind to Hendra and Nipah viruses and/or inhibit Hendra and Nipah virus activities.

BACKGROUND OF THE INVENTION

Nipah virus (NiV) and Hendra virus (HeV) are closely related paramyxoviruses that comprise the Henipavirus genus (Anonymous 1999 *MMWR Morb Mortal Wkly Rep* Ward, J. W. ed. 48:335-337; Chew, M. H. et al. 2000 *J Infect Dis* 181:1760-1763; Chua, K. B. et al. 2000 *Ann Neurol* 48:802-805; Eaton, B. T. 2001 *Microbes Infect* 3:277-278; Goh, K. J. et al. 2000 *N Engl J Med* 342:1229-1235; Lee, K. E. et al. 1999 *Ann Neurol* 46:428-432; Lim, C. C. et al. 2000 *Am J Neuroradiol* 21:455-461; Murray, K. et al. 1995 *Science* 268:94-97). Paramyxoviruses are negative-sense RNA containing enveloped viruses and encompass a variety of important human and animal pathogens, including measles virus, mumps virus, Sendai virus, Newcastle disease virus, rinderpest virus, canine distemper virus, human parainfluenza viruses, respiratory syncytial virus, and simian virus 5 (reviewed in Lamb and Parks, 2007, *Fields Virology*, eds. Knippe & Howley, Lippincott, Williams & Wilkins, pp. 1449-1496).

Like other paramyxoviruses, HeV and NiV possess two major membrane-anchored glycoproteins in the envelope of the viral particle. One glycoprotein is required for host cell receptor recognition and attachment and is designated as either a hemagglutinin-neuraminidase protein (HN), a hemagglutinin protein (H), or in the case of henipaviruses, a glycoprotein (G), which has neither hemagglutination nor neuraminidase activities. The other major glycoprotein is the fusion (F) glycoprotein, which is a trimeric class I fusogenic envelope glycoprotein containing two heptad repeat (HR) regions and a hydrophobic fusion peptide (Fp). The henipavirus F glycoprotein is synthesized as a precursor $F_0$ that undergoes posttranslational cleavage by host cell Cathepsin L that occurs within the endosomal compartment, most likely during endocytosis and recycling of F to the mature fusiogenic $F_1$ (a larger carboxy terminal fragment)+$F_2$ (a smaller amino terminal fragment) subunits that are held together by disulfide bonds through conserved cystine residues. See Pager, C. T. et al. 2006. *Virology* 346: 251-7; Pager, C. T. et al. 2005. *J Virol* 79: 12714-20; Meulendyke, K. A. et al. 2005, *J Virol*, 79: 12643-9; Diederich, S. M. et al. 2005, *J Biol Chem*, 280: 29899-903. In the mature form of F, the Fp's are situated at the N terminal of $F_1$ followed by the first HR (HRA) and the second HR (HRB) is located at the C terminus of $F_1$ preceding its transmembrane domain (reviewed in Lamb and Parks, 2007, *Fields Virology*, eds. Knippe & Howley, Lippincott, Williams & Wilkins, pp. 1449-1496).

Following attachment to host receptor ephrin (EFN) B2 or B3 via the G glycoprotein, HeV and NiV infect cells through a pH-independent membrane fusion process. This process is still poorly understood and is believed to involve conformational changes in G upon receptor binding that leads to activation and triggering of F. Lamb, R. A. et al. 2006, *Virology*, 344:30-7; Steffen, D. L. et al. 2012, *Viruses*, 4:280-308. Upon triggering, F undergoes significant conformational rearrangements that facilitate the insertion of the fusion peptide into target membranes, bringing the two HR regions together in the formation of the six-helix bundle structure or trimer-of-hairpins during or immediately following fusion of virus and cell membranes. The F driven membrane fusion process is thought to involve an irreversible folding from a metastable form followed by subsequent discrete conformational changes to a lower energy state. Several molecular details of this F re-folding upon triggering have been revealed in the structural solutions of both post- and pre-fusion conformations of respirovirus F. Yin, H. S. et al. 2005, *Proc Natl Acad Sci USA*, 102(26): 9288-93; Yin, H. S. et al. 2006, *Nature* 439:38-44.

Although currently there are no clinically approved vaccines or therapeutics against HeV or NiV, a Henipavirus G glycoprotein specific neutralizing monoclonal antibody (mAb) m102.4 was shown to protect African green monkey against HeV from lethal disease when it was administered as late as 72 hours post infection. Bossart, K. N. et al. 2011, *Sci Transl Med*, 3:105ra103. Antibodies or antibody fragments, such as monoclonal antibodies (mAbs) and fragments thereof, can be useful in elucidating the structure of a protein and understanding the function associated with various domains as well as providing a potential reagent for use as prophylaxis and/or therapeutic agents as in the case of the anti G m102.4. To date, there are very few reported anti henipavirus F mAbs and none are produced from recombinant protein. Aguilar, H. C. et al. 2007, *J Virol*, 81:4520-32; Guillaume, V. H. et al. 2006, *J Virol*, 80:1972-8. These reports provide limited information concerning the specific properties of the isolated antibodies. The development of a neutralizing anti-F antibodies and antibody fragments could serve as another potential henipavirus infection therapeutic agent perhaps more effectively when combined with m102.4. The anti-F antibodies and antibody fragments could also provide valuable tool to facilitate in structural and functional characterization of F mediated fusion in henipaviruses.

Therefore, the development of neutralizing or inhibiting antibodies and antibody fragments against NiV and HeV could have important implications for prophylaxis and passive immunotherapy. In addition, the characterization of the epitopes of the antibodies and antibody fragments and the mechanisms of neutralization and inhibition of NiV and HeV infection could provide helpful information for development of candidate vaccines and drugs. Finally, such antibodies and antibody fragments could also be used for diagnosis and as research reagents.

SUMMARY OF THE INVENTION

The present invention relates to antibodies or antibody fragments that bind, neutralize, and/or inhibit Hendra and/or Nipah virus. In particular, the present invention provides an antibody or fragment thereof that selectively binds a Hendra virus or Nipah virus F glycoprotein, wherein said antibody comprises: a heavy chain variable region comprising at least one complementarily-determining region (CDR) having the amino acid sequence selected from the group consisting of SEQ ID NO: 35, 37 and 39; and a light chain variable region comprising at least one CDR having the amino acid sequence selected from the group consisting of SEQ ID NO: 43, 45 and 47. The invention also provides a humanized antibody or antibody fragment selectively binding to a Hendra virus or Nipah virus F glycoprotein, wherein said antibody or antibody fragment comprises a heavy chain variable region having at least 90% sequence identity to SEQ ID NO: 33.

BRIEF DESCRIPTION OF THE DRAWINGS

FIG. 1A Amino acid sequence of $V_H$ and $V_L$ of m563. The CDR regions are labeled and underlined and the framework regions (FR) are also marked. The peptide and fragment sequences are shown by SEQ ID NO: 1-16, as listed in Table A. FIG. 1B The $V_H$ and $V_L$ of m563, humanized 5B3 (h5B3) and humanized 563.1 (h5B3.1) are separated by a flexible linker (e.g. a connector peptide -(G$_4$S)$_3$—) and inserted into a promoter enhanced pcDNA vector with a hygromycin selection marker, an Immunoglobulin light chain (Ic) leader sequence (Igκ lead) at the construct N terminal, an S peptide tag (Stag), and a hexa histidine tag (His) at the C terminal.

FIG. 2A-2B. Binding of murine 5B3 (m5B3), humanized 5B3 (h5B3), and humanized 5133.1 (h5B3.1) with F. FIG. 2A Binding of m5B3, h5B3, and h5B3.1 ScFv with soluble (sF) and full length (FL) F. FIG. 2B The ScFv constructs of m5B3, h5B3, and h5B3.1 as shown in FIG. 1B were transfected into 293T cells and supernatant was harvested at 48 hr post transfection. A human ScFv from a human ScFv library was used as control (ctrl). Equal amount of supernatant was added with sF protein or FL F expressing cell lysate and precipitated (IP) with Ni$^{2+}$ beads or S protein agarose as indicated. (B) Binding of h5B3, and h5B3.1 IgG with FL F. The human anti HeV G mAb, m102.4 which has the same Fc and CL fragment was used as control mAb. Purified mAb, each 2 µg, were added to FL F expressing cell lysate followed by precipitation with protein G Sepharose. In all cases, the precipitated products were analyzed on SDS PAGE followed by western blotting and the blots were probed (IB) with appropriate antibodies to detect the bands as indicated. IP: Immunoprecipitate; IB: Immuno blot; H: Heavy chain; L: Light chain.

FIG. 3A-B. Alignment of framework regions (FR) of m5B3 and h5B3 with that of human ScFv library and VH sequence of h5B3.1. FIG. 3A The FR's of VH and VL of m5B3 were aligned with that of human ScFv library and conserved human residues were identified as indicated by vertical arrows above the alignment. These conserved residues were then replaced into m5B3 homologous positions to produce FR's of h5B3 as shown at the first row of the alignment. (Upper panel: SEQ ID NO: 53 combined VH FR regions of h5B3; SEQ ID NO: 54 combined VH FR regions of m5B3; SEQ ID NO: 55-66 human ScFv library clones containing combined VH FR regions. Lower panel: SEQ ID NO: 67 combined VL FR regions of h5B3; SEQ ID NO: 68 combined VL FR regions of m5B3; SEQ ID NO: 69-80 human ScFv library clones containing combined VL FR regions). FIG. 3B Amino acid sequence of h5B3.1. SEQ ID NO: 31. The CDR regions are labeled and underlined. Highlighted residues in CDR indicate the amino acids that were mutated in h5B3 to generate h5B3.1.

FIG. 4A PCR primers with Xho I sites flanking the light and heavy chain ORF of pDR12 as shown by arrows were used to amplify the pDR12 h5B3.1 plasmid DNA, the PCR product was then digested and inserted into the Xho I site in the promoter enhanced pcDNA3.I Hygro(+) as shown. FIG. 4B Purified mAbs as indicated, 4 µg each, were analyzed on SDS PAGE followed by coomassie blue staining. Vertical arrows indicate the heavy (H) and light (L) chains of the mAbs. MW: Molecular weight marker.

FIG. 6A-B. Binding of NiV and CedPV F chimeras with different anti NiV F mAbs and fusion activities of the chimeras. FIG. 6A Cell lysates expressing different S peptide tagged NiV and CedPV F chimeras were precipitated with different anti NiV F mAbs or S protein agarose as indicated. The precipitated products were analyzed on SDS PAGE followed by western blotting and the blots were probed with anti S peptide Ab. Top band right below the 64 kDa marker is $F_0$ and lower band right below the 51 kDa marker is $F_1$. The schematic diagrams of the chimeras are shown on the right of the blots where stippled and clear indicate CedPV and NiV F regions. 1E11, 12132, and 5B3 are murine mAbs against the F glycoprotein. FIG. 6B Different NiV and CedPV F chimeras were tested for their ability to promote cell fusion in a p-Gal reporter cell fusion assay by co-expressing with NiV G in receptor negative HeLa-USU cells using permissive HeLa-ATCC cells as the target population. Assays were performed in triplicate, and fusion results were calculated and expressed as mean rates of (3-Gal activity (change in optical density at 570 nm per minute×1,000). Ni: NiV; Ce: CedPV; Hd: globular head of F; HRB: heptad repeat B of F.

FIG. 7A Precipitation and western blot analysis of murine 5B3 defective F mutants. A panel of S peptide tagged NiV F mutants were generated and expressed in 293T cells. The F expressing cell lysates were divided equally and precipitated with 5B3, 1262, and S protein agarose separately. The mAb-F complex was then added with protein G Sepharose. The precipitated products were analyzed on SDS PAGE followed by western blotting and the blots were probed with anti S peptide Ab. Top band is $F_0$ and lower band is $F_1$. FIG. 7B Fusion activity of 5B3 defective NiV F mutants in a β-Gal reporter cell fusion assay. The mutants of NiV F shown in FIG. 7A were tested for their ability to promote cell fusion by co-expressing with NiV G in receptor negative HeLa-USU cells using permissive HeLa-ATCC cells as the target population. The data shown are the mean percentage of WT fusion levels measured for each mutant calculated from three separate experiments normalized with total expression as measured by densitometry of western blot bands. The bars represent the range from multiple experiments. WT: wild type F. FIG. 7C Location of 5B3 epitope mapped to NiV F trimer structure displayed as surface representation. Stippled residues mark those that were mutated in this study. FIG. 7D Zoom in image of FIG. 7C labeling all residues tested in this study.

FIG. 8A-8C. Mechanism of 5B3 inhibition. FIG. 8A sF was cleaved by trypsin to produce mature $F_1+F_2$ and protease inhibitor was added to stop the reaction. 2 µg of biotinylated FC2 peptide was added with different amount of mAbs as indicated. The samples were then heated to 50° C. for 15 min to trigger F. The FC2-sF complex was then precipitated with avidin agarose. FIG. 8B Assay was carried out as described in FIG. 8A with m5B3 and h5B3.1, the unbound material from the 5 µg mAb reaction (4th lane from left) was collected and precipitated with protein G Sepharose (5ht lane from left). FIG. 8C Assay was carried out as described in FIG. 8A with 2 µg of mAb and increasing temperature as indicated for the heat treatment. The unbound material from all reactions was collected and precipitated with protein G Sepharose. In all the above cases, precipitated products were analyzed on SDS PAGE followed by western blotting and the blots were probed with anti-F rabbit antibody to detect F.

Figures 1A, 1B:
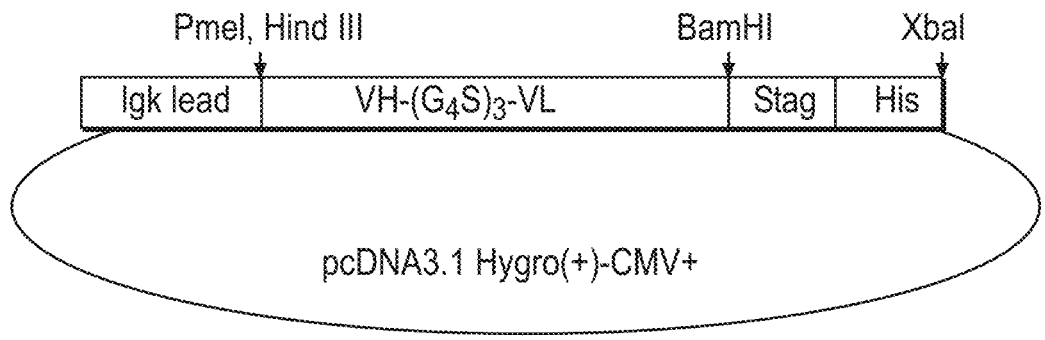
FIG. 1A-B. Amino acid sequence of m563 and ScFv construct cartoon.

comprise one heavy chain variable region ($V_H$) that is important for binding antigen and the light chain may comprise one light chain variable region ($V_L$) that is important for binding the antigen.

The Fab fragment (fragment antigen-binding) is a region of an antibody that binds to antigens. Fab may comprise one constant and one variable domain of each of the heavy and the light chain. These domains shape the paratope—the antigen-binding site—at the amino terminal end of the monomer. The two variable domains bind the epitope on their specific antigens. F(ab')$_2$ refers to an antibody fragment comprising a dimer of Fab. Fab and F(ab')$_2$ may be generated by recombinant technology or by cleavage of an antibody or a fragment of antibody. As is known in the art, only a portion of an antibody molecule, the paratope, is involved in the binding of the antibody to the epitopes of the antigen. The pFc' and Fc regions (fragment crystallizable region), for example, are effectors of the complement cascade but are not involved in antigen binding.

As used here, an ScFv (single-chain variable fragment) is a fusion peptide of the variable regions of the heavy ($V_H$)

TABLE A

Brief Description of m5B3, h5B3, and h5B3.1 SEQ ID NOs.

| | Heavy Chain SEQ ID NOs | | | | | | | Light Chain SEQ ID NOs | | | | | | |
|---|---|---|---|---|---|---|---|---|---|---|---|---|---|---|
| Fab/mab | $V_H$ | FR1 | CDR1 | FR2 | CDR2 | FR3 | CDR3 | FR4 | $V_L$ | FR1 | CDR1 | FR2 | CDR2 | FR3 | CDR3 | FR4 |
| m5B3 | 1 | 2 | 3 | 4 | 5 | 6 | 7 | 8 | 9 | 10 | 11 | 12 | 13 | 14 | 15 | 16 |
| h5B3 | 17 | 18 | 19 | 20 | 21 | 22 | 23 | 24 | 25 | 26 | 27 | 28 | 29 | 30 | 31 | 32 |
| h5B3.1 | 33 | 34 | 35 | 36 | 37 | 38 | 39 | 40 | 41 | 42 | 43 | 44 | 45 | 46 | 47 | 48 |

DETAILED DESCRIPTION OF THE PREFERRED EMBODIMENT

Definitions

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology* 3$^{rd}$ ed., J. Wiley & Sons, Chichester, N.Y., 2001, and *Fields Virology* 4$^{th}$ ed., Knipe D. M. and Howley P. M. eds, Lippincott Williams & Wilkins, Philadelphia 2001.

As used herein, the term "antibody" refers to an immunoglobulin molecule that may have the ability to specifically bind to a particular antigen. Antibodies may have different varieties known as isotypes or classes, such as but not be limited to the five basic antibody isotypes known as IgA, IgD, IgE, IgG and IgM. An antibody fragment may comprise a part of an immunoglobulin molecule or a combination of parts of immunoglobulin molecules. Antibody fragments may retain antigen binding ability. Antibody fragment may include antigen binding active fragments such as but not be limited to the well-known active fragments F(ab')$_2$, Fab, Fv, Fc, and Fd as well as fushion peptide such as ScFv. Antibodies and antibody fragments are well known to those of ordinary skill in the science of immunology. Antibodies and antibody fragments are regularly employed for both in vitro and in vivo studies and processes.

As used here, the terms "heavy chain" and "light chain" refer to the well-known immunoglobulin subunits and as part of an antibody and the fragments of the subunits. In their complete forms, the heavy chain is generally a longer polypeptide than the light chain. The heavy chain may and light chains ($V_L$) of immunoglobulins, connected with a connector or linker peptide. In some embodiments, the connector peptide ranges from about two to about 50 amino acids. In some embodiments, the connector peptide ranges from about ten to about 25 amino acids. The ScFv may retain the antigen binding ability of the original immunoglobulin molecule. Here an ScFv is considered an antibody fragment.

As used here, the Fd fragment may comprise the heavy chain portion of a Fab fragment. The Fd fragment may be produced by enzymatic cleavage or recombination technologies. In some embodiments, the Fd fragments are the major determinant of antibody specificity (a single Fd fragment may be associated with up to ten different light chains without altering antibody specificity) and Fd fragments retain epitope-binding ability in isolation.

Complementarity determining regions (CDRs) are peptide regions within the antigen-binding portion of an antibody. CDRs may directly interact with the epitope of the antigen and are the main determinant of antibody specificity. The framework regions (FRs) are peptide regions in the antigen-binding portion of the antibody that maintain the tertiary structure of the paratope. In some embodiments, in both the heavy chain variable region ($V_H$) and the light chain variable region ($V_L$), there are four framework regions (FR1 through FR4) separated respectively by three complementarity determining regions (CDR1 through CDR3). The CDRs, and in particular the CDR3 regions, and more particularly the heavy chain CDR3, may be largely responsible for antibody specificity.

As used herein, the terms "Hendra Virus Disease" and "Nipah Virus Disease" refer to diseases caused, directly or indirectly, by infection with Hendra or Nipah virus. The broad species tropisms and the ability to cause fatal disease in both animals and humans have distinguished Hendra virus (HeV) and Nipah virus (NiV) from all other known paramyxoviruses (Eaton B. T. 2001 *Microbes Infect* 3:277-278). These viruses can be amplified and cause disease in large animals and can be transmitted to humans where infection is manifested as a severe respiratory illness and/or febrile encephalitis.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the polynucleotide and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein, "sequence identity" is a measure of the identity of nucleotide sequences or amino acid sequences compared to a reference nucleotide or amino acid sequence. A polypeptide having an amino acid sequence at least, for example, about 95% "sequence identity" to a reference an amino acid sequence, e.g., SEQ ID NO: 1, is understood to mean that the amino acid sequence of the polypeptide is identical to the reference sequence except that the amino acid sequence may include up to about five modifications per each 100 amino acids of the reference amino acid sequence. In other words, to obtain a peptide having at least about 95% sequence identity to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

In general, the sequences are aligned so that the highest order match is obtained. "Sequence identity" per se has an art-recognized meaning and can be calculated using well known techniques. While there are several methods to measure identity between two polynucleotide or polypeptide sequences, the term "identity" is well known to skilled artisans (Carillo (1988) J. Applied Math. 48, 1073). Examples of computer program methods to determine sequence identity and similarity between two sequences include, but are not limited to, GCG program package (Devereux (1984) Nucleic Acids Research 12, 387), BLASTP, ExPASy, BLASTN, FASTA (Atschul (1990) J. Mol. Biol. 215, 403) and FASTDB. Examples of methods to determine sequence identity and similarity are discussed in Michaels (2011) Current Protocols in Protein Science, Vol. 1, John Wiley & Sons.

In one embodiment of the present invention, the algorithm used to determine sequence identity between two or more polypeptides is BLASTP. In another embodiment of the present invention, the algorithm used to determine sequence identity between two or more polypeptides is FASTDB, which is based upon the algorithm of Brutlag (1990) Comp. App. Biosci. 6, 237-245). In a FASTDB sequence alignment, the query and reference sequences are amino sequences. The result of sequence alignment is in percent sequence identity. In one embodiment, parameters that may be used in a FASTDB alignment of amino acid sequences to calculate percent sequence identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent sequence identity. For query sequences truncated at the N- or C-termini, relative to the reference sequence, the percent sequence identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent sequence identity, calculated by the above FASTDB program using the specified parameters, to arrive at a final percent sequence identity score. This corrected score can be used for the purposes of determining how alignments "correspond" to each other, as well as percentage sequence identity. Residues of the reference sequence that extend past the N- or C-termini of the query sequence may be considered for the purposes of manually adjusting the percent sequence identity score. That is, residues that are not matched/aligned with the N- or C-termini of the comparison sequence may be counted when manually adjusting the percent sequence identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent sequence identity score calculated by the FASTDB program. If the remaining 90 residues were perfectly matched (100% alignment) the final percent sequence identity would be 90% (100% alignment−10% unmatched overhang). In another example, a 90 residue query sequence is compared with a 100 reference sequence, except that the deletions are internal deletions. In this case the percent sequence identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent sequence identity. The addition in the query occurs at the N-terminus of the query sequence and therefore, the FASTDB alignment may not show a match/alignment of the first 10 residues at the N-terminus. If the remaining 100 amino acid residues of the query sequence have 95% sequence identity to the entire length of the reference sequence, the N-terminal addition of the query would be ignored and the percent identity of the query to the reference sequence would be 95%.

As used here, the term "conservative substitution" denotes the replacement of an amino acid residue by another biologically similar residue. Conservative substitution for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below in Table I.

TABLE I

Conservative Substitutions

| Side Chain Characteristic | Amino Acid |
| --- | --- |
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) *Biochemistry*, Second Edition; Worth Publishers, pp. 71-77, as set forth below in Table II.

TABLE II

Conservative Substitutions

| Side Chain Characteristic | Amino Acid |
| --- | --- |
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hydroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic): | Asp, Glu |

And still other alternative, exemplary conservative substitutions are set out below in Table III.

TABLE III

Conservative Substitutions

| Original Residue | Exemplary Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |

TABLE III-continued

Conservative Substitutions

| Original Residue | Exemplary Substitution |
| --- | --- |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

As used herein with respect to polypeptides and polynucleotides, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated polynucleotide is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a polynucleotide sequence existing in its native state in its natural host is not. An isolated polypeptide and polynucleotide may be substantially purified, but need not be. For example, a polynucleotide that is isolated within a cloning or expression vector is not pure in that it may comprise only a tiny percentage of the material in the cell in which it resides. Such a polynucleotide is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of polynucleotides into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. In some embodiments, the vectors are capable of autonomous replication and expression of the structural gene products present in the DNA segments to which they are operably joined.

Novel Anti-HeV and NiV F Glycoprotein Antibodies or Antibody Fragment

The present invention derives, in part, from the development, isolation and characterization of novel antibodies or antibody fragments that selectively bind to and inhibit Hendra and Nipah viruses. As described more fully below, these antibodies or antibody fragments have been shown to bind the F glycoprotein and to reduce or block the infection of Hendra and Nipah viruses. The paratope of the anti-HeV and NiV Fab fragments associated with the neutralization epitopes on the HeV and NiV glycoprotein F are defined by the amino acid (aa) sequences of the immunoglobulin heavy and light chain regions described in Table A and SEQ ID NO: 1 through SEQ ID NO: 48. Additional antibodies, antibody fragments, and related sequences are disclosed by SEQ ID NO: 49-80.

In some embodiments, the present invention provides the full-length antibodies or antibody fragments thereof selectively binding to Hendra and Nipah F glycoproteins in isolated form and in pharmaceutical preparations. Similarly, as described below, the present invention provides isolated polynucleotides, vectors, host cells transformed with the polynucleotides, and compositions and pharmaceutical preparations including isolated polypeptides, which encode the full-length Hendra and Nipah F glycoprotein antibodies and/or antibody fragments. Finally, the present invention provides methods, as described more fully below, employing these antibodies and polynucleotides in the in vitro and in vivo diagnosis, prevention and therapy of Hendra Virus Disease or Nipah Virus Disease.

The complete amino acid sequences of the antigen-binding Fab portions of the Hendra and Nipah monoclonal antibodies m5B3 (murine 5B3), h5B3 (humanized 5B3) and h5B3.1 (humanized 5B3.1) as well as the relevant $V_H$, $V_L$, FR and CDR regions are listed in Table A and disclosed herein. SEQ ID NOs: 1, 17 and 33 disclose the amino acid sequences of the Fd fragment of the Hendra and Nipah monoclonal antibodies. The amino acid sequences of the heavy chain FR1, CDR1, FR2, CDR2, FR3, CDR3 and FR4 regions are disclosed as (FR1, SEQ ID NOs: 2, 18 and 34); (CDR1, SEQ ID NOs: 3, 19 and 35); (FR2, SEQ ID NOs: 4, 20 and 36); (CDR2, SEQ ID NOs: 5, 21 and 37); (FR3, SEQ ID NOs: 6, 22 and 38); (CDR3, SEQ ID NOs: 7, 23 and 39); and (FR4, SEQ ID NOs: 8, 24 and 40). SEQ ID NOs: 9, 25 and 41 disclose the amino acid sequences of the light chain variable fragments of the Hendra and Nipah antibodies. The amino acid sequences of the light chain FR1, CDR1, FR2, CDR2, FR3, CDR3 and FR4 regions are disclosed as (FR1, SEQ ID NOs: 10, 26 and 42); (CDR1, SEQ ID NOs: 11, 27 and 43); (FR2, SEQ ID NOs: 12, 28 and 44); (CDR2, SEQ ID NOs: 13, 29 and 45); (FR3, SEQ ID NOs: 14, 30 and 46); (CDR3, SEQ ID NOs: 15, 31 and 47); (FR4, SEQ ID NOs: 16, 32 and 48).

It is now established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human Thus, as will be apparent to one of ordinary skill in the art, the present invention also provides for F(ab')$_2$, Fab, Fv, Fd and ScFv fragments of Hendra and Nipah F glycoprotein antibodies; chimeric antibodies in which the Fc and/or FR1 and/or FR2 and/or FR3 and/or FR4 and/or CDR1 and/or CDR2 and/or CDR3 regions of the Hendra and Nipah antibodies have been replaced by homologous human or non-human sequences; chimeric F(ab')$_2$ fragments in which the FR1 and/or FR2 and/or FR3 and/or FR4 and/or CDR1 and/or CDR2 and/or CDR3 regions of the Hendra and Nipah F glycoprotein antibodies have been replaced by homologous human or non-human sequences; chimeric Fab fragments in which the FR and/or CDR1 and/or CDR2 and/or CDR3 regions have been replaced by homologous human or non-human sequences; chimeric Fd fragment antibodies in which the FR1 and/or FR2 and/or FR3 and/or FR4 and/or CDR1 and/or CDR2 and/or CDR3 regions have been replaced by homologous human or non-human sequences; and ScFv in which the FR1 and/or FR2 and/or FR3 and/or FR4 and/or CDR1 and/or CDR2 and/or CDR3 regions have been replaced by homologous human or non-human sequence. Thus, those skilled in the art may alter the Hendra and Nipah antibodies by the construction of CDR grafted or chimeric antibodies or antibody fragments containing all, or part thereof, of the disclosed heavy and light chain V-region CDR amino acid sequences (Jones, P. T. et al. 1986 Nature 321:522-525; Verhoeyen, M. et al. 1988 Science 39:1534-1536; and Tempest, P. R. et al. 1991 Biotechnology 9:266-271), without destroying the specificity of the antibodies for the F glycoprotein epitope. Such FR or CDR grafted or chimeric antibodies or antibody fragments can be effective in prevention and treatment of Hendra or Nipah virus infection in animals (e.g., horses) and man.

In some embodiments, the antibodies and/or antibody fragments may be produced in which some or all of the FR regions of the Hendra and Nipah F glycoprotein antibodies have been replaced by other homologous human FR regions. In addition, the Fc portions may be replaced so as to produce IgA or IgM as well as IgG antibodies bearing some or all of the CDRs of the Hendra and Nipah F glycoprotein antibodies. Of particular importance is the inclusion of the Hendra and Nipah F glycoprotein antibody heavy chain CDRs, to a lesser extent, the other CDRs of the Hendra and Nipah F glycoprotein antibodies. Such humanized antibodies and/or antibody fragments have particular utility in that they do not evoke an immune response against the antibody itself.

The current invention discloses an antibody or antibody fragment thereof that selectively binding a Hendra virus or Nipah virus F glycoprotein, wherein said antibody comprises: a heavy chain variable region comprising at least one complementarily-determining region (CDR) having the amino acid sequence selected from the group consisting of SEQ ID NO: 3, 5, 7, 19, 21, 23, 35, 37 and 39; and a light chain variable region comprising at least one CDR having the amino acid sequence selected from the group consisting of SEQ ID NO: 11, 13, 15, 27, 29, 31, 43, 45 and 47. In particular, the current invention discloses an antibody or antibody fragment thereof that selectively binds a Hendra virus or Nipah virus F glycoprotein, wherein said antibody comprises: a heavy chain variable region comprising at least one complementarily-determining region (CDR) having the amino acid sequence selected from the group consisting of SEQ ID NO: 35, 37 and 39; and a light chain variable region comprising at least one CDR having the amino acid sequence selected from the group consisting of SEQ ID NO: 43, 45 and 47.

The current invention discloses an antibody or antibody fragment that may comprise a heavy chain CDR1 comprising the amino acid sequence of SEQ ID NO: 35, an antibody or antibody fragment that may comprise a heavy chain CDR2 comprising the amino acid sequence of SEQ ID NO: 37; and/or an antibody or antibody fragment that may comprise a heavy chain CDR3 comprising the amino acid sequence of SEQ ID NO: 39. In addition, the current invention discloses an antibody or antibody fragment that may comprise a light chain CDR1 comprising the amino acid sequence of SEQ ID NO: 43, an antibody or antibody fragment that may comprise a light chain CDR2 comprising the amino acid sequence of SEQ ID NO: 45; and/or an antibody or antibody fragment that may comprise a light chain CDR3 comprising the amino acid sequence of SEQ ID NO: 47.

The current invention discloses an antibody or antibody fragment comprising a heavy chain variable region with at least 80%, 85%, 90%, 91%, 92%, 93%, 94%, 95%, 96%, 97%, 98% or 99% sequence identity to SEQ ID NO: 1, 17 or 33. The current invention discloses an antibody or antibody fragment comprising a heavy chain variable region with the amino acid sequence of SEQ ID NO: 1, 17 or 33. In some embodiments, the antibody fragment is an ScFv, Fab, F(ab')$_2$, or Fd.

The current invention discloses an antibody or antibody fragment comprising a light chain variable region with at least 90% or 99% sequence identity to SEQ ID NO: 19, 25 or 41. The current invention discloses an antibody or antibody fragment comprising a light chain variable region with the amino acid sequence of SEQ ID NO: 9, 25 or 41. In some embodiments, the antibody fragment is an ScFv, Fab, or F(ab')$_2$.

The current invention discloses an antibody or antibody fragment comprising a heave chain variable region with the amino acid sequence of SEQ ID NO: 1, 17 or 33, and a light chain variable region with the amino acid sequence of SEQ ID NO: 9, 25 or 41.

The current invention discloses an antibody or antibody fragment selectively binding to Hendra virus or Nipah virus F glycoprotein, wherein said antibody or antibody fragment comprises a heavy chain comprising one or more amino acid sequences selected from the group consisting of: FR1 region comprising SEQ ID NO: 2, 18 or 34, FR2 region comprising SEQ ID NO: 4, 20 or 36, FR3 region comprising SEQ ID NO: 6, 22 or 38, and FR4 region comprising SEQ ID NO: 8, 24 or 40. In addition, the current invention discloses an antibody or antibody fragment selectively binding to Hendra virus or Nipah virus F glycoprotein, wherein said antibody or antibody fragment comprises a light chain comprising one or more amino acid sequences selected from the group consisting of: FR1 region comprising SEQ ID NO: 10, 26 or 42, FR2 region comprising SEQ ID NO: 12, 28 or 44, FR3 region comprising SEQ ID NO: 14, 30 or 46, and FR4 region comprising SEQ ID NO: 16, 32 or 48.

In some embodiments, the current invention discloses an ScFv antibody fragment comprising a $V_H$ and a $V_L$ having a sequence selected from the group consisting of: SEQ ID NO: 1, 17, 33, 9, 25, and 41. The $V_H$ and $V_L$ may be connected by a connector peptide with a length of 2-50 amino acids. In some embodiments, the ScFv fragment may comprise a $V_H$ of SEQ ID NO: 33 and a $V_L$ of SEQ ID NO: 41, wherein the connector peptide may comprise 10-25 amino acids. In some embodiments, the connector peptide may comprise SEQ ID NO: 52.

In some embodiments, the invention relates to an antibody or antibody fragment that selectively binds to Hendra virus or Nipah virus F glycoprotein, wherein said antibody or antibody fragment comprises a heavy chain comprising one or more amino acid sequences selected from the group consisting of: FR1 region comprising SEQ ID NO: 34, FR2 region comprising SEQ ID NO: 36, FR3 region comprising SEQ ID NO: 38, and FR4 region comprising SEQ ID NO: 40, and a light chain comprising one or more amino acid sequences selected from the group consisting of: FR1 region comprising SEQ ID NO: 42, FR2 region comprising SEQ ID NO: 44, FR3 region comprising SEQ ID NO: 46, and FR4 region comprising SEQ ID NO: 48.

The current invention discloses a humanized antibody or antibody fragment selectively binding to a Hendra virus or Nipah virus F glycoprotein, wherein said antibody or antibody fragment comprises a heavy chain variable region having at least 80%, 85%, 90%, 91%, 92%, 93%, 94%, 95%, 96%, 97%, 98% or 99% sequence identity to SEQ ID NO: 17 or 33. In some embodiments, the antibody or antibody fragment comprises a heavy chain variable region having the amino acid sequence of SEQ ID NO: 17 or 33. The current invention discloses a humanized antibody or antibody fragment selectively binding to a Hendra virus or Nipah virus F glycoprotein, wherein said antibody or antibody fragment comprises a light chain variable region having at least 80%, 85%, 90%, 91%, 92%, 93%, 94%, 95%, 96%, 97%, 98% or 99% sequence identity to SEQ ID NO: 25 or 41. In some embodiments, the antibody or antibody fragment comprises a light chain variable region having the amino acid sequence of SEQ ID NO: 25 or 41.

In some embodiments, the current invention discloses an antibody comprising heavy and/or light chain variable regions with 80%, 85%, 90%, 91%, 92%, 93%, 94%, 95%, 96%, 97%, 98% or 99% sequence identity to the heavy and/or light chain variable regions of the antibody encoded on the plasmids contained in FreeStyle™ 293 cells deposited as American Type Culture Collection (ATCC) deposit PTA-120575. In some embodiments, the current invention discloses an antibody comprising heavy and light chain variable regions with identical sequences to the heavy and light chain variable regions of the antibody encoded on the plasmids contained in FreeStyle™ 293 cells deposited as American Type Culture Collection (ATCC) deposit PTA-120575.

The current invention discloses a humanized antibody or antibody fragment selectively binding to a Hendra virus or Nipah virus F glycoprotein eiptope, wherein said antibody or antibody fragment inhibits Hendra or Nipah virus infection. The current invention discloses a humanized antibody or antibody fragment selectively binding to a Hendra virus or Nipah virus F glycoprotein eiptope, wherein said antibody or antibody fragment disrupts virus host membrane fusion. The current invention discloses a humanized antibody or antibody fragment selectively binding to a Hendra virus or Nipah virus F glycoprotein eiptope, wherein said antibody or antibody fragment blocks F glycoprotein folding. In some embodiments, the antibody or antibody fragment inhibits Hendra or Nipah virus infection by disrupting virus host membrane fusion. In some embodiments, the antibody or antibody fragment disrupts virus host membrane fusion by blocking F glycoprotein folding.

It is also possible, in accordance with the present invention, to produce chimeric antibodies or antibody fragments including non-human sequences. Thus, one may use, for example, murine, ovine, equine, bovine or other mammalian Fc or FR sequences to replace some or all of the Fc or FR regions of the Hendra and Nipah F glycoprotein antibodies. Some of the CDRs may be replaced as well. Such chimeric antibodies or antibody fragments bear non-human immunoglobulin sequences admixed with the CDRs of the human Hendra and Nipah F glycoprotein antibodies. These antibodies or antibody fragments may be used, among others, for brief periods or in immunosuppressed individuals. Hendra and Nipah viruses also infect animals and such antibodies may be used for brief periods or in immunosuppressed subjects.

For inoculation or prophylactic uses, in some embodiments, the antibodies of the present invention are full-length antibody molecules including the Fc region. Such full-length antibodies may have longer half-lives than smaller antibody fragments (e.g., Fab) and are more suitable for intravenous, intraperitoneal, intramuscular, intracavity, subcutaneous, or transdermal administration.

In some embodiments, Fab fragments and other antibody fragments, including not limited to chimeric Fab fragments, may be used. Fabs offer several advantages over $F(ab')_2$ and whole immunoglobulin molecules for this therapeutic modality. First, because Fabs have only one binding site for their cognate antigen, the formation of immune complexes is precluded whereas such complexes can be generated when bivalent $F(ab')_2$'s and whole immunoglobulin molecules encounter their target antigen. This is of some importance because immune complex deposition in tissues can produce adverse inflammatory reactions. Second, because Fab fragments lack an Fc region they generally cannot trigger adverse inflammatory reactions that are activated by Fc, such as activation of the complement cascade. Third, the tissue penetration of the small Fab molecule is likely to be much better than that of the larger whole antibody. Fourth, Fab fragments can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fab fragments, smaller antibody fragments and epitope-binding peptides having binding specificity for the epitopes defined by the Hendra and Nipah antibodies can also be used to bind or inhibit the virus. For example, single chain antibodies can be constructed according to the method of U.S. Pat. No. 4,946,778, to Ladner et al. Single chain antibody fragments (e.g. ScFv) comprise the variable regions of the light and heavy chains joined by a flexible linker moiety. Yet smaller is the antibody fragment known as the single domain antibody or Fd, which comprises an isolated $V_H$ single domain. Techniques for obtaining a single domain antibody with at least some of the binding specificity of the full-length antibody from which they are derived are known in the art.

It is possible to determine, without undue experimentation, if an altered or chimeric antibody or antibody fragment has the same specificity as the Hendra and Nipah antibodies by ascertaining whether the former blocks the latter from binding to F glycoprotein. If the antibody or fragment thereof being tested competes with a known Hendra or Nipah antibody as shown by a decrease in binding of the Hendra or Nipah antibody, then it is likely that the two antibodies and/or antibody fragments bind to the same, or a closely spaced, epitope. Still another way to determine whether an antibody has the specificity of known Hendra and Nipah antibodies or antibody fragments is to pre-incubate the known Hendra or Nipah antibody with F glycoprotein with which it is normally reactive, and then add the antibody or antibody fragment being tested to determine if the antibody or antibody fragment being tested is inhibited in its ability to bind F glycoprotein. If the antibody or antibody fragment being tested is inhibited then, in all likelihood, it is likely that it has the same, or a functionally equivalent, epitope and specificity as the known Hendra and Nipah antibodies or antibody fragments of the invention. Screening of Hendra and Nipah antibodies or antibody fragments also can be carried out by utilizing Hendra or Nipah viruses and determining whether the mAb neutralizes the virus.

By using the antibodies or antibody fragments of the invention, it is now possible to produce anti-idiotypic antibodies or antibody fragments which can be used to screen other antibodies or antibody fragments to identify whether the antibody or antibody fragment has the same binding specificity as an antibody of the invention. In addition, such antiidiotypic antibodies or antibody fragments can be used for active immunization (Herlyn, D. et al. 1986 *Science* 232:100-102). Such anti-idiotypic antibodies or antibody fragments can be produced using well-known hybridoma techniques (Kohler, G. and Milstein, C. 1975 *Nature* 256: 495-497). An anti-idiotypic antibody or antibody fragment is an antibody or antibody fragment which recognizes unique determinants present on the antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the antibody or antibody fragment of interest. The immunized animal will recognize and respond to the idiotypic determinants of the immunizing antibody and produce an antibody to these idiotypic determinants. By using the anti-idiotypic antibodies or antibody fragments of the immunized animal, which are specific for the antibodies or antibody fragments of the invention, it is possible to identify other clones with the same idiotype as the antibody or antibody fragment of the hybridoma used for immunization. Idiotypic identity between antibodies or antibody fragments of two cell lines demonstrates that the two antibodies and/or antibody fragments are the same with respect to their recognition of the same epitopic determinant. Thus, by using anti-idiotypic antibodies or antibody fragments, it is possible to identify other hybridomas expressing antibodies or antibody fragments having the same epitopic specificity.

It is also possible to use the anti-idiotype technology to produce antibodies or antibody fragments which mimic an epitope. For example, an anti-idiotypic antibody or antibody fragment made to a first antibody will have a binding domain in the hypervariable region which is the image of the epitope bound by the first antibody. Thus, the anti-idiotypic antibody can be used for immunization, since the anti-idiotype antibody binding domain effectively acts as an antigen.

In some embodiments, the current invention relates to F glycoprotein antibodies and or antibody fragments comprising heavy chain variable regions and/or light chain variable regions and conservative substitutions thereof. The specific sequences of the antibodies or antibody fragments are described above. In one aspect, the substitutions are conservative in nature; however, the invention embraces substitutions that are also non-conservative.

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces FGFBP3 or variants thereof that have been covalently modified to include one or more water-soluble polymer attachments such as polyethylene glycol, polyoxyethylene glycol or polypropylene glycol.

Polynucleotides Encoding Anti-HeV and NiV F Glycoprotein Antibodies or Antibody Fragments Given the disclosure herein of the amino acid sequences of the heavy chain Fd and light chain variable domains of the Hendra and Nipah antibodies or antibody fragments against the F glycoprotein, one of ordinary skill in the art is now enabled to produce polynucleotides which encode this antibody or which encode the various antibody fragments or chimeric antibodies described above. It is contemplated that such polynucleotides will be operably joined to other polynucleotides forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the Hendra and Nipah antibodies, including framework and CDRs or parts thereof, and a suitable promoter either with (Whittle, N. et al. 1987 *Protein Eng* 1:499-505 and Burton, D. R. et al. 1994 *Science* 266:1024-1027) or without (Marasco, W. A. et al. 1993 *Proc Natl Acad Sci USA* 90:7889-7893 and Duan, L. et al. 1994 *Proc Natl Acad Sci USA* 91:5075-5079) a signal sequence for export or secretion. Such vectors may be transformed or transfected into prokaryotic (Huse, W. D. et al. 1989 *Science* 246:1275-1281; Ward, S. et al. 1989 *Nature* 341:544-546; Marks, J. D. et al. 1991 *J Mol Biol* 222:581-597; and Barbas, C. F. et al. 1991 *Proc Natl Acad Sci USA* 88:7978-7982) or eukaryotic (Whittle, N. et al. 1987 *Protein Eng* 1:499-505 and Burton, D. R. et al. 1994 *Science* 266:1024-1027) cells or used for gene therapy (Marasco, W. A. et al. 1993 *Proc Natl Acad Sci USA* 90:7889-7893 and Duan, L. et al. 1994 *Proc Natl Acad Sci USA* 91:5075-5079) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

In some embodiments, the vector for screening antibodies or antibody fragment may be a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector may or may not include DNA regulatory sequences for expressing the fusion polypeptide, e.g. prokaryotic regulatory sequences. Such vectors can be constructed by those with skill in the art and have been described by Smith, G. P. et al. (1985, *Science* 228: 13151317); Clackson, T. et al. (1991, *Nature* 352:624-628); Kang et al. (1991, *Methods: A Companion to Methods in Enzymology*, vol. 2, R. A. Lerner and D. R. Burton, ed. Academic Press, NY, pp 111-118); Barbas, C. F. et al. (1991, *Proc Natl Acad Sci USA* 88:7978-7982); Roberts, B. L. et al. (1992, *Proc Natl Acad Sci USA* 89:2429-2433).

A fusion polypeptide may be useful for purification of the antibodies or antibody fragments of the invention. The fusion domain may, for example, include a poly-His tail which allows for purification on $Ni^{+}$ columns or the maltose binding protein of the commercially available vector pMAL (New England BioLabs, Beverly, Mass.). In some embodiments, the fusion domain is a filamentous phage membrane anchor. This domain is particularly useful for screening phage display libraries of monoclonal antibodies but may be of less utility for the mass production of antibodies. In some embodiments, the filamentous phage membrane anchor is a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is generally a leader peptide domain of a protein that targets the protein to the membrane of the host cell, such as the periplasmic membrane of Gram-negative bacteria. In some embodiments, the secretion signal for *E. coli* is a pelB secretion signal. The leader sequence of the pelB protein has previously been used as a secretion signal for fusion proteins (Better, M. et al. 1988 *Science* 240:1041-1043; Sastry, L. et al. 1989 *Proc Natl Acad Sci USA* 86:5728-5732; and Mullinax, R. L. et al., 1990 *Proc Natl Acad Sci USA* 87:8095-8099). Amino acid residue sequences for other secretion signal polypeptide domains from *E. coli* useful in this invention can be found in Neidhard, F. C. (ed.), 1987 in *Escherichia coli* and *Salmonella Typhimurium: Typhimurium Cellular and Molecular Biology*, American Society for Microbiology, Washington, D.C.

To achieve high levels of gene expression in *E. coli*, it may be necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine J. and Dalgarno L. 1975 *Nature* 254:34-38). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In some embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. In some embodiments, the origins of replication are those that are efficient in the host organism. In some embodiments, the host cell is *E. coli*. In some embodiments, for use of a vector in *E. coli*, the origin of replication is ColEI found in pBR322 and a variety of other common plasmids. In some embodiments, the origin is a p15A origin of replication found on pACYC and its derivatives. The ColEI and p15A replicons have been extensively utilized in molecular biology, are available on a variety of plasmids and are described by Sambrook et al., 1989, in *Molecular Cloning: A Laboratory Manual*, 2nd edition, Cold Spring Harbor Laboratory Press.

In addition, those embodiments that include a prokaryotic replicon may also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen (San Diego, Calif.).

When the antibodies or antibody fragments of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies or antibody fragments, such as the full-length antibodies of the invention or the ScFv, F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

In some embodiments, the vector comprises a first cassette that includes upstream and downstream DNA regulatory sequences operably joined via a sequence of nucleotides adapted for directional ligation to an insert DNA. The upstream translatable sequence may encode the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that may encode a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies or antibody fragments of the present invention may additionally be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies or antibody fragments of the present invention may furthermore be produced in plants. In 1989, Hiatt A. et al. 1989 *Nature* 342:76-78 first demonstrated that functional antibodies could be produced in transgenic plants.

Since then, a considerable amount of effort has been invested in developing plants for antibody (or "plantibody") production (for reviews see Giddings, G. et al. 2000 *Nat Biotechnol* 18:1151-1155; Fischer, R. and Emans, N. 2000 *Transgenic Res* 9:279-299). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-HeV and NiV F Glycoprotein Antibody Preparations The invention also relates to methods for preparing diagnostic or pharmaceutical compositions comprising the antibodies or antibody fragments of the invention or polynucleotide sequences encoding the antibodies or antibody fragments of the invention, the pharmaceutical compositions being used for immunoprophylaxis or immunotherapy of Hendra Virus Disease or Nipah Virus Disease. The pharmaceutical preparation includes a pharmaceutically acceptable carrier. Such carriers, as used herein, refers to a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The anti-Hendra and anti-Nipah F glycoprotein antibodies or antibody fragments of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the antibodies or antibody fragments of the invention, or will be able to ascertain such, using routine experimentation. Furthermore, the binding of these labels to the antibodies or antibody fragments of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise an antibody and/or antibody fragment of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The antibodies or antibody fragments of the invention are suited for in vitro use, for example, in immunoassays in which they can be utilized in liquid phase or bound to a solid phase carrier. In addition, the antibodies or antibody fragments in these immunoassays can be detectably labeled in various ways. Examples of types of immunoassays which can utilize the antibodies or antibody fragments of the invention are competitive and non-competitive immunoassays in either a direct or indirect format. Examples of such immunoassays are the radioimmunoassay (RIA) and the sandwich (immunometric) assay. Detection of antigens using the antibodies or antibody fragments of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies or antibody fragments of the invention can be bound to many different carriers and used to detect the presence of Hendra or Nipah virus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding antibodies, or will be able to ascertain such, using routine experimentation.

For purposes of the invention, Hendra or Nipah virus may be detected by the antibodies or antibody fragments of the invention when present in biological fluids and tissues. Any sample containing a detectable amount of Hendra or Nipah virus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of Hendra or Nipah Virus

In using the antibodies or antibody fragments of the invention for the in vivo detection of antigen, the detectably labeled antibody or antibody fragment is given in a dose which is diagnostically effective. The term "diagnostically effective" means that the amount of detectably labeled antibody is administered in sufficient quantity to enable detection of the site having the Hendra or Nipah virus antigen for which the antibodies are specific.

The concentration of detectably labeled antibody or antibody fragment which is administered should be sufficient such that the binding to Hendra or Nipah virus is detectable compared to the background. Further, it is desirable that the detectably labeled antibody or antibody fragment be rapidly cleared from the circulatory system in order to give the best target-to-background signal ratio.

As a rule, the dosage of detectably labeled antibody or antibody fragment for in vivo diagnosis will vary depending on such factors as age, sex, and extent of disease of the individual. The dosage of antibody or antibody fragment can vary from about 0.01 mg/kg to about 50 mg/kg, e.g. 0.1 mg/kg to about 20 mg/kg, or about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to antibodies or antibody fragments either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the antibodies of the invention are $^{111}$In, $^{97}$Ru, $^{67}$Ga, $^{68}$Ga, $^{72}$As, $^{89}$Zr and $^{201}$Tl.

The antibodies or antibody fragments of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The antibodies or antibody fragments of the invention can be used in vitro and in vivo to monitor the course of Hendra Virus Disease or Nipah Virus Disease therapy. Thus, for example, by measuring the increase or decrease in the number of cells infected with Hendra or Nipah virus or changes in the concentration of Hendra or Nipah virus present in the body or in various body fluids, it would be possible to determine whether a particular therapeutic regimen aimed at ameliorating Hendra Virus Disease or Nipah Virus Disease is effective.

Prophylaxis and Therapy of Hendra Virus Disease and Nipah Virus Disease

The antibodies or antibody fragments can also be used in prophylaxis and as therapy for Hendra Virus Disease and Nipah Virus Disease in both humans and other animals. The terms, "prophylaxis" and "therapy" as used herein in conjunction with the antibodies of the invention denote both prophylactic as well as therapeutic administration and both passive immunization with substantially purified polypeptide products, as well as gene therapy by transfer of polynucleotide sequences encoding the product or part thereof. Thus, the antibodies or antibody fragments can be administered to high-risk subjects in order to lessen the likelihood and/or severity of Hendra Virus Disease and Nipah Virus Disease or administered to subjects already evidencing active Hendra or Nipah virus infection. In the present invention, ScFv or Fab fragments also bind or neutralize Hendra or Nipah virus and therefore may be used to treat infections.

As used herein, a "prophylactically effective amount" of the antibodies or antibody fragments of the invention is a dosage large enough to produce the desired effect in the protection of individuals against Hendra or Nipah virus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, e.g. from about 0.1 mg/kg to about 20 mg/kg, or from about 0.2 mg/kg to about 2 mg/kg, in one or more administrations (priming and boosting).

As used herein, a "therapeutically effective amount" of the antibodies or antibody fragments of the invention is a dosage large enough to produce the desired effect in which the symptoms of Hendra Virus Disease or Nipah Virus Disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, e.g. from about 0.1 mg/kg to about 20 mg/kg, or from about 0.2 mg/kg to about 2 mg/kg, in one or more dose administrations daily, for one or several days. In some embodiments, the administration of the antibody is conducted for 2 to 5 or more consecutive days in order to avoid "rebound" of virus replication from occurring.

The antibodies or antibody fragments of the invention can be administered by injection or by gradual infusion over time. The administration of the antibodies or antibody fragments of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, Remington's Pharmaceutical Sciences, 18th edition, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and the like.

Generation of m5B3 ScFv, h5B3 and h5B3.1

Several soluble forms of NiV or HeV F (sF) were engineered and recombinant sF constructs were produced. Culture supernatant of stable 293T cells expressing the different forms of NiV and HeV sF was collected and clarified prior to affinity chromatography purification with S-protein agarose beads (Novagen Corp). The S agarose purified material was applied to HiLoad 16/60 Superdex 200 prep grade gel filtration column to isolate pure trimer. Balb/cJ mice (Jackson Laboratory) were inoculated with different purified soluble viral antigen as shown in table 1 for 4 times at 30 days intervals. When indicated the enzymatic S tag cleaved sF was used for immunization. Each mouse was bled prior to immunization to obtain serum (pre-bleed) as negative control. In a single immunization, each animal was given 12 µg of sF mixed with Sigma Adjuvant System™ (Sigma). Each immunization was given in a 0.1 ml dose administered through intraperitoneal and subcutaneous injections of 0.05 ml in each of 2 sites with a 25 ga. needle. Adjuvant and antigen formulations were made based on manufacturer's instructions. The mice were bled 7-10 days post 3rd immunization and serum samples were harvested. Four days before sacrificing the mice for the final bleed collection, another immunization was performed without adjuvant. All sF glycoprotein constructs elicit a strong antibody response among immunized mice. The ELISA endpoint titer of each mouse was greater than 1:320,000 in all cases and were able to precipitate native full length F expressed in HeLa cells. In most cases, the harvested serum from the immunized mice inhibits NiV and HeV virus infections.

One form of sF was produced by deleting the transmembrane (TM) and cytoplasmic tail (CT) domains and appending a trimeric coiled-coil (GCNt) domain. The GCNt-appended constructs ($sF_{GCNt}$) elicited cross-reactive henipavirus-neutralizing antibody in mice. In addition, $sF_{GCNt}$ constructs could be triggered in vitro by protease cleavage followed by heat treatment. A series of monoclonal antibodies (mAbs) were derived from mice that had been immunized with different sF's, e.g. the non-GCNt-appended NiV $sF_{dFp}$ and NiV $sF_{GCNt}$.

Lymphocytes from immunized mice were fused with the commercially available Sp2/0 cell line (murine myeloma cells) using high molecular weight polyethylene glycol (PEG) and hybridoma cells were selected according to standard practices. Lymphocytes fused with murine myeloma cells were selected for by passage of the cultures in medium with hypoxanthine, aminopterin, and thymadine supplement (HAT, Invirtogen). Hybridoma cell lines secreting antibody reactive with the viral antigen were identified by enzyme-linked immunosorbent assay (ELISA) using supernatant harvested from each well. Colonies secreting mAb which binds sF were isolated and subjected to limiting dilution at least two times to ensure clonality. Purified mAb was prepared from hybridoma cells grown to high density in SFM4MAb medium (Hyclone) supplemented with hypoxanthine and thymadine (HT, Invitrogen) and 100 U/ml recombinant mouse interleukin 6 (rl L-6, Roche Applied Biosciences). Antibody in the supernatant of spent cultures was purified using a Protein-G sepharose (GE Healthsciences) bead affinity chromatography. The concentration of each preparation was determined using Bradford assay.

Based on ELISA screening of the culture supernatant from the fusion plate, more than 60 hybridoma clones secreting antibodies reacting with sF were identified. 24 clones were selected for further purification via limiting dilution to generate stable hybridoma lines for mAb isolation and 19 of these mAbs were used for characterization. 18 mAbs are cross reactive for NiV and HeV F and 1 is NiV specific Among the mAb library, 13 were able to precipitate full length F and $sF_{GCNt}$ (pre-fusion F) and the remaining one precipitates only $sF_{dFp}$ (post-fusion F). Of the thirteen prefusion specific mAbs, 12 precipitated $F_0$ and $F_1$ and 1 mAb precipitated only $F_0$. This observation suggests a different conformation may be acquired by cleaved and un-cleaved F. Six of the mAbs that precipitated only post-fusion F were tested in western blot and found to recognize linear epitopes. Ten mAbs were tested in NiV and HeV pseudotyped virus entry inhibition, showed to inhibit entry and another additional two inhibit at higher concentration. One of the mAb (murine 5B3 or m5B3) was tested in live NiV and HeV infection and showed to neutralize at a concentration of 12.5 µg/ml for HeV and 1.5 µg/ml for NiV.

m5B3 was one of the F-specific mAbs. In addition, m5B3 was determined to recognize a conformation-dependent epitope and could also completely neutralize infectious $200TCID_{50}$ NiV and HeV at concentrations of 1.5 and 12.5 µg/ml, respectively. Using an immunoprecipitation followed by Western blot analysis, m5B3 was determined to bind only to NiV and HeV $sF_{GCNt}$ and the full-length wild-type NiV and HeV F-glycoprotein forms of both sF and native F that evidently exist in the pre-fusion conformational state.

The cDNA of 5B3 mouse hybridoma clone was synthesized and the variable regions of heavy ($V_H$) and light chain ($V_L$) sequences were amplified using several sets of universal primers, cloned, and sequenced (FIG. 1A). The peptide and fragment sequences in FIG. 1A are shown by SEQ ID NO: 1-16, as listed in Table A. A ScFv of murine 5B3 (m5B3), SEQ ID NO: 49, was then constructed with $V_H$ (SEQ ID NO: 1) and $V_L$ (SEQ ID NO: 9) connected by a connector peptide of $(G_4S)_3$, SEQ ID NO: 52, followed by S peptide and His tag in a promoter modified commercially available mammalian expression vector pcDNA 3.1 Hygro (+) (Invirogen Corp) (7) (FIG. 1B). Soluble ScFv of m5B3 was expressed in 293 FreeStyle™ suspension cell and purified using S agarose affinity column followed by size exclusion chromatography. FIG. 2A shows transient expressed m5B3 ScFv was able to bind to soluble (sF) and full length (FL) F.

Based on the conserved FR sequence of m5B3, a human ScFv library was constructed. The clones from this library were selected based on high level of expression in E. coli. The FR sequences of the selected human ScFv clones were aligned with that of m5B3 ScFv. The conserved human residues were identified and mutated in the m5B3 FR homologous positions producing a humanized 5B3 (h5B3) as shown in FIG. 3A. FIG. 3A, upper panel, SEQ ID NO: 53—combined $V_H$ FR regions of h5B3; SEQ ID NO: 54—combined $V_H$ FR regions of m5B3; SEQ ID NO: 55-66—human ScFv library clones containing combined $V_H$ FR regions as shown in FIG. 3A. FIG. 3A, lower panel, SEQ ID NO: 67—combined $V_L$ FR regions of h5B3; SEQ ID NO: 68—combined $V_L$ FR regions of m5B3; SEQ ID NO: 69-80—human ScFv library clones containing combined $V_L$ FR regions as shown in FIG. 3A.

The h5B3 ScFv was synthesized, cloned, expressed and purified the same way as m5B3 ScFv. The peptide and fragment sequences of h5B3 are shown by SEQ ID NO: 17-32, as listed in Table A. The h5B3 ScFv has a peptide sequence of SEQ ID NO: 50, wherein the $V_H$ (SEQ ID NO: 17) and $V_L$ (SEQ ID NO: 25) of h5B3 are connected by a connector peptide (SEQ ID NO: 52). Later another version of h5B3 was generated, which was named h5B3.1 where one residue on each of the complementarity-determining region (CDR) CDR1 and 2, and two residues on CDR3 were mutated into conserved human residues based on the sequence from the human ScFv library as mentioned above (FIG. 3B). The h5B3.1 was then expressed and purified as h5B3 ScFv. The peptide and fragment sequences of h5B3.1 are shown by SEQ ID NO: 33-48, as listed in Table A. The h5B3.1 ScFv has a peptide sequence of SEQ ID NO: 51, wherein the $V_H$ (SEQ ID NO: 33) and $V_L$ (SEQ ID NO: 41) of h5B3.1 are connected by a connector peptide (SEQ ID NO: 52).

As shown in FIG. 2A, both h5B3 and h5B3.1 were able to bind FL F.

Generation of h5B3 and h5B3.1 IgG1

Figures 4A, 4B:
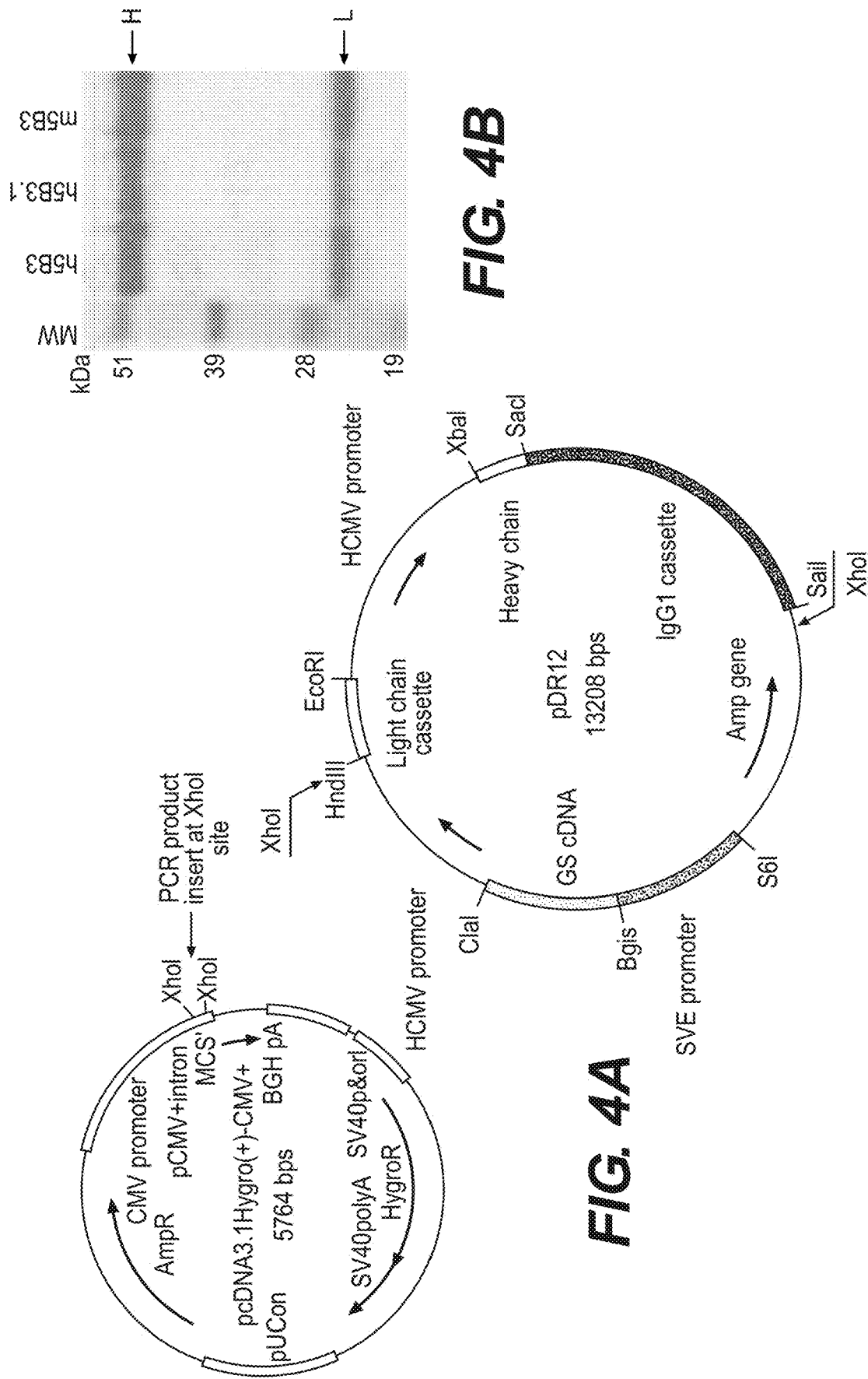
FIG. 4A-4B. Diagram of vectors used to produce h5B3.1 IgG1 in pcDNA and coomassie stain of purified m5B3, h5B3, and h5B3.1 IgG.

The $V_H$ and $V_L$ of both h5B3 and h5B3.1 were cloned into vector pDR12 to generate full IgG1. Both h5B3- and h5B3.1-IgG1 were then shown to bind to FL F (FIG. 2B). The open reading frames (ORF) of the heavy and light chain of h5B3.1 IgG1 were cloned into a promoter enhanced expression vector as shown in FIG. 4A and the construct was used to develop a stable 293 FreeStyle™ suspension cell line that produced high yield (approximately 8 mg/shaker flask) of h5B3.1 IgG1 in shaker flasks in serum free medium (FIG. 4B).

Freestyle™ cell line 293 cells that contain a plasmid encoding the h5B3.1 antibody were deposited as American Type Culture Collection (ATCC) deposit PTA-120575 on Aug. 29, 2013. The ATTC is located at 10801 University Boulevard, Manassas, Va. 20110.

The affinities of m5B3, h5B3- and h5B3.1-IgG1 were then determined as shown in Table 1, which demonstrate the binding kinetics of m5B3, h5B3, and h5B3.1 against sF.

a 96 well tissue culture plate. Viral cytopathic effect (cpe) was observed at 3 days post infection. The titer was determined as the highest dilution in which viral cpe was still fully inhibited (absent) in two wells. The assay was performed separately to compare between m5B3 and h5B3; and m5B3 and h5B3.1.

Characterization of 5B3 Binding and Mapping of 5B3 Epitope

Figure 5:
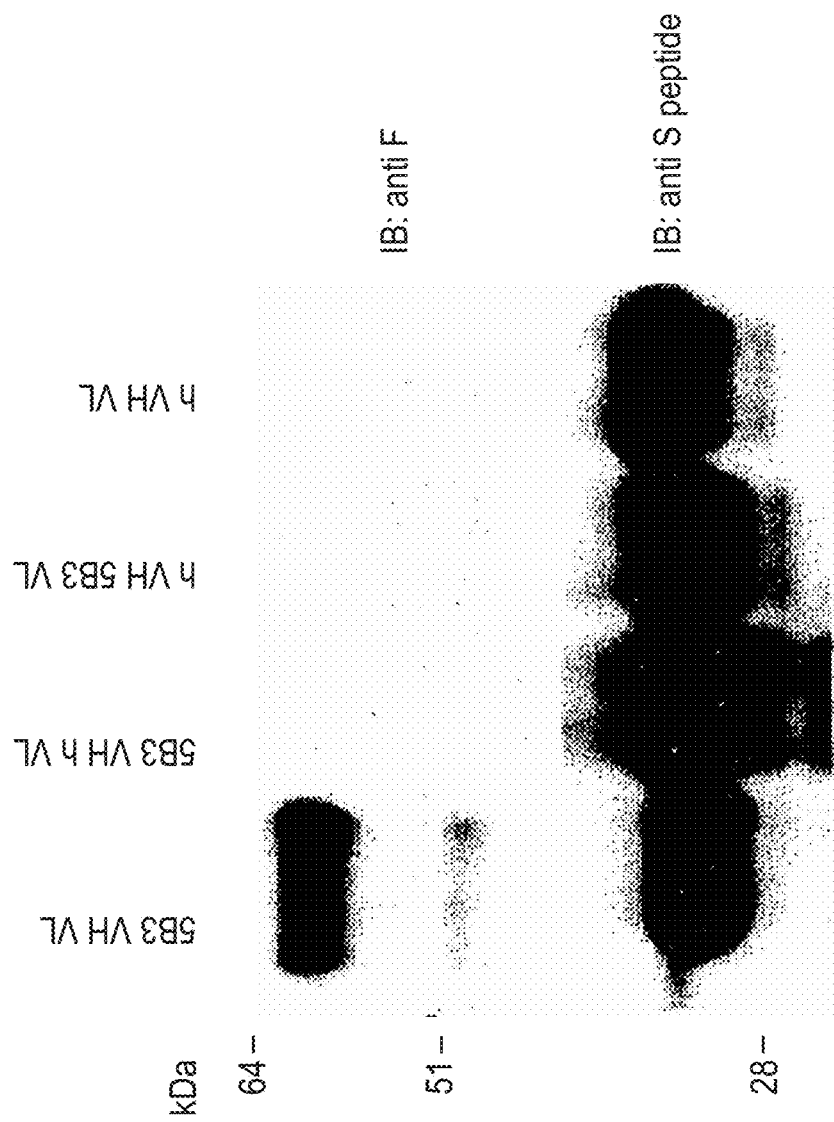
FIG. 5. Determination of 5B3 chain binding. Supernatant of cell expressing different S peptide tagged h5B3 and human ScFv VH VL chimeras as indicated were added to untagged F expressing cell lysate and precipitated with S protein agarose. The precipitated products were analyzed on SDS PAGE followed by western blotting and the blots were probed (IB) with anti S peptide antibody to detect the ScFv or anti-F antibody to detect F.

To determine if both heavy (H) and light (L) chain of 5B3 is involved in binding to F, chimeras of $V_H$ and $V_L$ of h5B3 and one of the clone from the human ScFv library (FIG. 3A) were constructed as in FIG. 1B. As shown in FIG. 5, none of the chimeras were able to bind FL F indicating that both H and L of 5B3 are involved in binding to F.

Next, to determine the location of 5B3 epitope on F, chimeras of NiV F and the F protein of Cedar virus (CedPV), a newly discovered henipavirus (Marsh, G. A. et al. 2012, *PLoS Pathog,* 8:e1002836 in which 5B3 does not react with were generated. Only the construct that possesses the globular head domain of NiV F and HRB helical stem, TM and CT of CedPV F was able to bind to 5B3 (FIG. 6) indicating that the epitope is located at the globular head domain. The head and HRB chimeras were also shown to be functional in a cell-cell fusion assay.

TABLE 1

Binding kinetic analysis of m5B3, h5B3, and h5B3.1 against soluble F

| mAb | ka (l/Ms) | kd (l/s) | Rmax (RU) | Concentration of sF | KA (l/M) | KD (M) | $\chi^2$ |
|---|---|---|---|---|---|---|---|
| m5B3 | $3.4 \times 10^4$ | $9.2 \times 10^{-5}$ | 36.1 | 0-200 nM | $3.7 \times 10^8$ | $2.7 \times 10^{-9}$ | 0.04 |
| h5B3 | $2.5 \times 10^4$ | $3.3 \times 10^{-4}$ | 22.9 | 0-379 nM | $7.5 \times 10^7$ | $1.3 \times 10^{-8}$ | 0.03 |
| h5B3.1 | $2.7 \times 10^4$ | $1.7 \times 10^{-3}$ | 24.1 | 0-279 nM | $1.6 \times 10^7$ | $6.2 \times 10^{-8}$ | 0.04 |

Table 1 shows the binding kinetic analysis of m5B3, h5B3, and h5B3.1 against soluble F. Biacore analysis was performed by A&G Precision Antibody™ (Columbia, Md.) using Biacore 3000. Certificate grade CM5 chips were coated with capture antibody (goat anti-mouse IgG Fc for mouse mAb and goat anti-human IgG Fc for humanized mAb). The test mAb was then captured on the chip and the binding kinetics were measured at 5 different sF concentrations (from 0 to saturating). Binding kinetic parameters at each sF concentration were measured and a $\chi 2$ analysis was performed to assess the accuracy of the data.

In addition, both h5B3- and h5B3.1-IgG1 were shown to inhibit live NiV and HeV at similar titers as compared to m5B3 (Table 2).

TABLE 2

Virus neutralization by m5B3, h5B3, and h5B3.1

| | Titer (μg/ml) 200 TCID50 | | Titer (μg/ml) 100 TCID50 | |
|---|---|---|---|---|
| mAb | NiV | HeV | NiV | HeV |
| m5B3 | 1.56 | 12.5 | 0.78 | 1.56 |
| h5B3 | 3.125 | 12.5 | | |
| h5B3.1 | | | 1.56 | 0.78 |
| m6D3 | >100 | >100 | >100 | >100 |

Table 2 shows virus neutralization by m5B3, h5B3, and h5B3.1. Purified mAb were serial diluted in duplicate by doubling dilution starting at 100 μg/ml and incubated with NiV or HeV separately at 37° C. for 30 min. The virus-mAb mixture was then used to infect $2\times10^4$ Vero cells per well of A NiV F mutant, L53D was shown to be defective in binding to 5B3. Based on the solved crystal structure of sF, residues surrounding L53 were mutated to alanine for hydrophilic and/or hydrophobic residues and/or serine for hydrophobic residues (Table 3) from a WT F construct that has a C-terminal S peptide tag.

TABLE 3

Summary of F mutants reactivity with 5B3 and 12B2.

| | | Binding to mAb | |
|---|---|---|---|
| Residue | Change to | 5B3 | 12B2 |
| N51 | A | ++ | ++ |
| L53 | D | -- | ++ |
| | S | -- | ++ |
| P52 | A | ++ | ++ |
| T54 | A | ++ | ++ |
| K55 | A | -- | ++ |
| | E | -- | ++ |
| D56 | A | -- | -- |
| E166 | A | ++ | ++ |
| K167 | A | ++ | ++ |
| R244 and T245 | A and S | ++ | ++ |
| L246 | A | ++ | ++ |
| | D | -- | -- |
| | S | +/- | +/- |
| G247 | A | ++ | ++ |
| | S | ++ | ++ |
| L246 and G247 | D and A | -- | -- |
| G247 and Y248 | S and S | ++ | ++ |

TABLE 3-continued

Summary of F mutants reactivity with 5B3 and 12B2.

| | | Binding to mAb | |
| --- | --- | --- | --- |
| Residue | Change to | 5B3 | 12B2 |
| Y248 | A | ++ | ++ |
| | S | ++ | ++ |
| Y248 and A249 | D and A | -- | ++ |
| A249 | D | +/- | ++ |
| | S | ++ | ++ |
| T250 | A | -- | ++ |
| E251 | A | ++ | ++ |
| Y281 | A | ++ | ++ |
| F282 | A | + | ++ |
| | S | ++ | ++ |
| P283 | A | ++ | ++ |
| | S | + | + |
| F282 and P283 | A and A | -- | -- |
| I284 | S | ++ | ++ |
| E251 and I284 | A and S | -- | ++ |

Figure 7A:
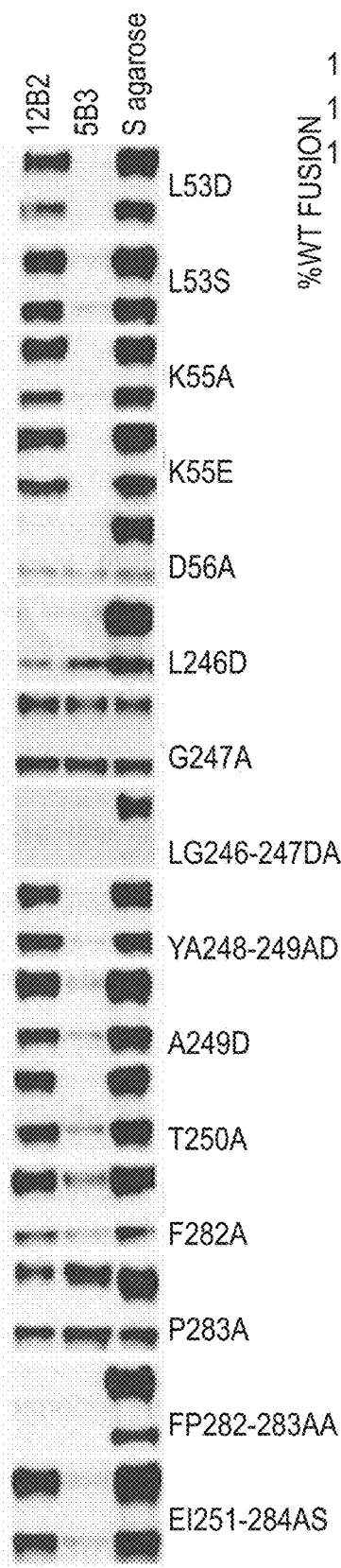
FIG. 7A-D. Mapping of 5B3 epitope by mutagenesis.
Figure 7B:
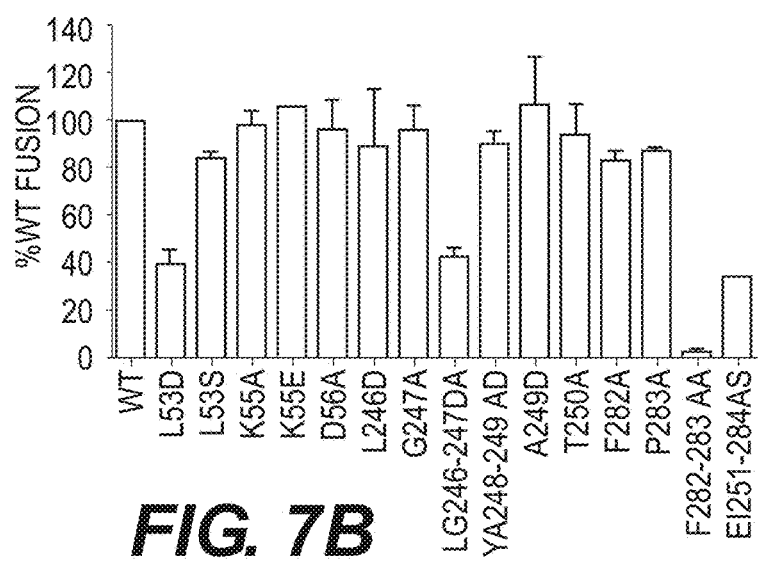
Figure 7C:
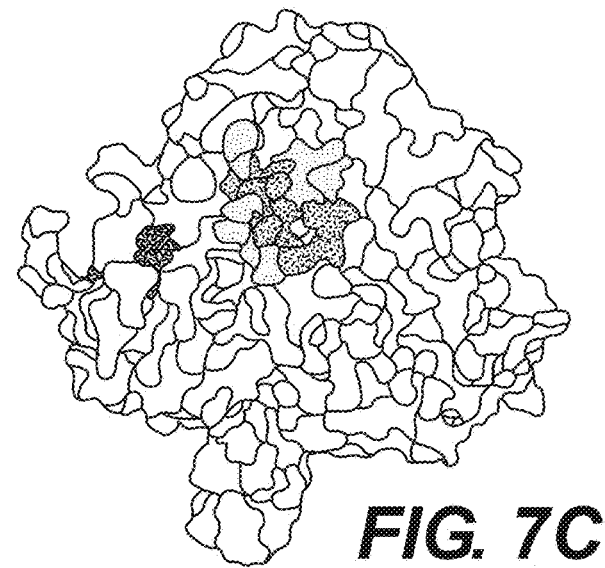
Figure 7D:
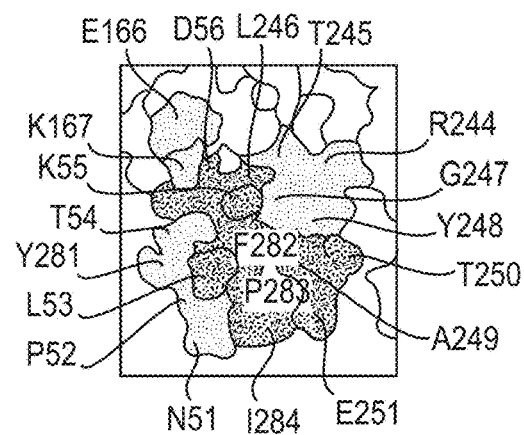

Table 3 provides a summary of F mutants' reactivities with 5B3 and 12B2, another conformational dependent neutralizing mAb. Residues surrounding L53 as shown in FIG. 7C were mutated to alanine for hydrophilic residues and/or serine for hydrophobic residues. Single and double F mutants were then tested for their binding with 5B3 by precipitating the F expressing cell lysate separately with 5B3 and 12B2 by protein G Sepharose and S protein agarose. The precipitated products were analyzed on SDS PAGE followed by western blotting. The F bands were detected using HRP conjugated anti S peptide antibody. ++: strong binding; +: less binding; +/-: weak binding; --: no binding.

The F mutants were then tested for their binding with 5B3 by precipitating F expressing cell lysates with 5B3 and another conformational dependent neutralizing mAb, 12B2 to determine if the F mutant is conformational intact. Equal amount of F expressing cell lysate was precipitated with S protein agarose to monitor total expression. A summary of the result is shown in table 3 and western blot of selected mutants shown in FIG. 7A. The experiment identified several single F mutants (L53D/S, K55A/E, T250A) and two double mutants (YA248-249AD and E1251-284AS) that are defective in binding to 5B3 but has no effect on 12B2 binding indicating the location of 5B3 epitope is at the side of the globular head (FIG. 7). Although mutant Y248A alone had no effect on 5B3 binding, when combined with mutant A249D that is almost defective (faint band when precipitated by 5B3), the double mutant is completely defective in 5B3 binding showing that both residues are important in the binding site. Similarly, mutants E251A and I284S are only defective when combined. Mutant F282A showed a slight decrease in 5B3 binding, although completely defective when combined with P283A, this double mutant is also defective in 12B2 binding. Several other 5B3 defective mutants (D56A, L246D, and LG246-247DA) were also defective in 12B2 binding (FIG. 7A, Table 3). Therefore, these mutants together with those that are only 5B3 defective were tested in a fusion assay to test for their ability in promoting cell fusion. As mentioned above mutant L53D is less efficient in promoting fusion, combining mutants L246D and G247A also showed less than 50% of fusion activity compared to wild type (WT) indicating a compromise in function. Only mutant FP282-283AA was completely defective in fusion indicating that this double mutant is not conformational and functional intact. Mutants D56A and L246D probably have an indirect effect on 12B2 binding that has no effect on F function in promoting fusion. All other tested mutants retains more than 80% of fusion activity except E1251-284AS having less than 40% activity as compared to WT although maintaining its binding with 12B2 (FIG. 7B). Residues E251 and I284 probably are involved in F protein function in promoting fusion and perhaps mutation on these residues affect the protein functionally rather than conformationally as seen by mutant L53D.

Taken together, the location of 5B3 epitope is at the side of the globular head in a region involving residues L53, K55, Y248, A249, T250, E251, I284, F282 and possibly residues D56, and L246 (FIGS. 7C and D).

Mechanism of 5B3 Inhibition

The mechanism of 5B3 inhibition in F fusion was also investigated. An in vitro sF triggering assay was previously developed (Chan, Y. P. et al. 2012, J Virol. 86: 11457-71) where sF can be triggered by trypsin digestion to its mature F1+F2 form followed by heat treatment that will trigger sF to re-fold into its post fusion conformation. A biotinylated peptide with the HRB sequence of F (FC2) can be added to the trypsin digested F1+F2 that will bind to the intermediate form of the triggering F during heat treatment and the intermediate form can then be precipitated by avidin agarose. When 5B3 was added together with FC2 peptide, the mAb can compete with FC2 to bind to the triggering sF in a dose dependent manner (FIG. 8A). The unbound material from this assay was then precipitated with protein G and FIG. 8B shows that both m563 and h563.1 were still bound to sF. Since 5B3 only binds to pre-fusion F, this indicates that when 5B3 was present during triggering, the mAb stabilizes and held sF in its pre-fusion form. To investigate this further, the triggering was then conducted with varying increasing temperatures in order to provide more energy to force triggering in the presence of 5B3. As shown in FIG. 8C, increasing temperatures were able to recover FC2 precipitation of the intermediate form, indicating that binding of 5B3 stabilizes F by creating a higher energy barrier for triggering to occur.

The results here showed that 5B3 binds to the side of the globular head of F revealing a novel epitope that could be a region important for stabilizing F. One of the residue shown here to be important for 5B3 binding, L53 was also shown to be an important residue for the formation of hexameric trimers of F on virus surface which is required for efficient fusion where triggering of a single trimeric F could produce a chain effect on the hexamer. Binding of 5B3 to F may also interfere with this chain triggering effect rendering viral fusion inefficient.

Potential Uses of the Antibodies and Antibody Fragments Against F Glycoprotein

The immediate application of the 5B3 is as a tool for Henipavirus research. For example, no mAbs are currently available to detect and differentiate pre and post fusion F. 5B3 recognizes a conformation-dependent epitope and can be used to distinguish pre and post fusion F. These assays are useful in studying the functional and structural characteristics of the glycoprotein following manipulation, such as conformational changes occurring in F following G receptor binding. The need for additional diagnostic and detection material for Henipaviruses has arisen from routine epidemics occurring at greater distances from the original disease epicenters. Given that Henipaviruses exhibit a broad species tropism of these viruses and the zoonotic origin of the viruses often involving domesticated animals in the transmission to humans, diagnostic and detection techniques should be robust and suitable for use with samples from many species. Early detection of the Henipaviruses could provide sufficient notice to institute control measures capable of reducing morbidity and mortality. Initial diagnosis of disease emanating from infection with a Henipavirus is dependent on clinical illness and epidemiologic characteristics. The diagnosis is later confirmed by the identification of the virus at a reference laboratory. 5B3 could be used in the development of a cheap and rapid diagnostic/detection tool that would be of sufficient specificity and sensitivity to provide early warning to the presence of a Henipavirus.

One of the most promising uses h5B3 and h5B3.1 is in the development of additional therapeutic agents for treating Henipavirus infection. These humanized mAb can be expressed, purified in large scale, and used as an antiviral agent without the risk of complications from idiotypic responses in the recipient. The data from live virus SNT indicated that 5B3 is a potent inhibitor of NiV and HeV F mediated fusion. Development of h5B3 and/or h5B3.1 as therapeutic agents in combination with the anti G human m102.4 mAb as a cocktail therapy would help minimize the development of viral resistance to the therapy by simultaneously targeting independent epitopes of the two glycoproteins.

The Henipaviruses are some of the most pathogenic and highly fatal emerging viral diseases that have been recognized. Significant advances have been made in the study and control of these viruses, but additional research is ongoing. A humanized antivirus mAb has been developed to target the Henipavirus F glycoprotein that have broad applicability in research as well as clinical application. As seen, 5B3 target a conformation-dependent pre fusion specific epitope. Mapping of the 5B3 binding region revealed a novel epitope that is important for stabilizing F. The humanized h5B3.1 maintained all binding activities with F as well as virus neutralizing titer as compared to m5B3. The optimized expression system of h5B3.1 IgG1 developed here provided easy, fast and high yield production of the humanized mAb. Further development of h5B3.1 is required and on-going, for example mutagenesis on the CDR regions to improve its binding affinity with F as well as testing its potency in protecting disease in animal models, but the potential benefits and commercial uses are clearly evident.

What is claimed is:

1. A method of treating a Hendra Virus Disease or a Nipah Virus Disease comprising administering to a human subject a therapeutically effective amount of an antibody or fragment thereof that selectively binds a Hendra virus or Nipah virus F glycoprotein, wherein said antibody comprises:
- a heavy chain variable region comprising complementarily-determining regions (CDRs) having the amino acid sequence of SEQ ID NO: 35 for CDR1, 37 for CDR2 and 39 for CDR3; and
- a light chain variable region comprising CDRs having the amino acid sequence of SEQ ID NO: 43 for CDR1, 45 for CDR2 and 47 for CDR3.

2. The method of claim 1 wherein said antibody or antibody fragment comprises an Fd fragment.

3. The method of claim 1 wherein said antibody fragment is a Fab fragment.

4. The method of claim 1 wherein said antibody fragment is a single chain variable fragment (ScFv).

5. The method of claim 4 wherein the ScFv further comprises a connector peptide.

6. The method of claim 5 wherein the connector peptide comprises the amino acid sequence of SEQ ID NO: 52.

7. The method of claim 4 wherein the ScFv comprises SEQ ID NO: 51.

8. The method of claim 1 wherein said antibody or antibody fragment comprises a variable heavy chain which comprises the amino acid sequence of SEQ ID NO: 33.

9. The method of claim 1 wherein said or antibody fragment antibody comprises a variable light chain which comprises the amino acid sequence of SEQ ID NO: 41.

10. A method of treating a Hendra Virus Disease or a Nipah Virus Disease comprising administering to a human subject a therapeutically effective amount of a humanized antibody or antibody fragment selectively binding to a Hendra virus or Nipah virus F glycoprotein, wherein said antibody or antibody fragment comprises a heavy chain variable region comprising the amino acid sequence of SEQ ID NO: 33 and a light chain variable region comprising the amino acid sequence of SEQ ID NO: 41.

11. The method of claim 10, wherein the antibody is an IgG1.

12. The method of claim 10, wherein said antibody or antibody fragment inhibits Hendra or Nipah virus infection.

13. The method of claim 12, wherein said antibody or antibody fragment inhibits Hendra or Nipah virus infection by disrupting virus host membrane fusion.

14. The method of claim 13, wherein said antibody or antibody fragment disrupts virus host membrane fusion by blocking F glycoprotein re-folding.

15. An antibody comprising heavy and light chain variable regions identical in sequence to the antibody encoded on the plasmids contained in the FreeStyle™ 293 cells deposited as American Type Culture Collection (ATCC) deposit PTA-120575.

16. The antibody of claim 15, wherein the antibody inhibits Hendra or Nipah virus infection by blocking F glycoprotein folding during virus host membrane fusion.

* * * * *